(12) United States Patent
Lee et al.

(10) Patent No.: US 9,145,442 B2
(45) Date of Patent: Sep. 29, 2015

(54) **CYCLIC PENTADEPSIPEPTIDES AND MICROORGANISM OF *FUSARIUM* STRAIN PRODUCING THE SAME**

(71) Applicant: Chung-Ang University Industry-Academy Cooperation Foundation, Seoul (KR)

(72) Inventors: Chan Lee, Gyeonggi-Do (KR); Hyuk-Hwan Song, Seoul (KR); Hee-Seok Lee, Seoul (KR)

(73) Assignee: Chung-Ang University Industry-Academy Cooperation Foundation, Seoul (KR)

( * ) Notice: Subject to any disclaimer, the term of this patent is extended or adjusted under 35 U.S.C. 154(b) by 0 days.

(21) Appl. No.: 14/502,520

(22) Filed: Sep. 30, 2014

(65) Prior Publication Data

US 2015/0025219 A1  Jan. 22, 2015

Related U.S. Application Data

(63) Continuation of application No. 12/600,830, filed as application No. PCT/KR2009/000005 on Jan. 2, 2009.

(51) Int. Cl.
| | | |
|---|---|---|
| *A61K 38/12* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 11/02* | (2006.01) |
| *C12P 21/02* | (2006.01) |
| *C12R 1/77* | (2006.01) |
| *A61K 38/15* | (2006.01) |
| *A61K 38/00* | (2006.01) |

(52) U.S. Cl.
CPC ............... *C07K 11/02* (2013.01); *A61K 38/15* (2013.01); *C12P 21/02* (2013.01); *C12R 1/77* (2013.01); *A61K 38/00* (2013.01)

(58) Field of Classification Search
CPC ....... A61K 38/00; A61K 38/15; C07K 11/02; C12P 21/02; C12R 1/77
See application file for complete search history.

(56) References Cited

PUBLICATIONS

Belofsky et al. Sansalvamide: A New Cytotoxic Cyclic Depsipeptide Produced by a Marine Fungus of the Genus *Fusarium*. Tetrahedron Letters, 1999. vol. 40, pp. 2913-2916.*
Song et al. A new cytotoxic cyclic pentadepsipeptide, neo-N-methylsansalvamide produced by *Fusarium solani* KCCM90040, isolated from potato. May 15, 2011, vol. 126, Issue 2, pp. 472-478.*
Song et al. Diversity in Beauvericin and Enniatins H, I, and MK1688 by *Fusarium oxysporum* isolated from potato. International Journal of Food Microbiology. Mar. 20, 2008, vol. 122, pp. 296-301.*

* cited by examiner

*Primary Examiner* — Marcela M Cordero Garcia
(74) *Attorney, Agent, or Firm* — Mintz Levin Cohn Ferris Glovsky and Popeo, P.C.; Kongsik Kim

(57) ABSTRACT

Disclosed is a *Fusarium* strain producing novel cyclic pentadepsipeptides which are of excellent multidrug resistance-reversing activity and inhibitory activity against cancer cells. Also, novel cyclic pentadepsipeptides are provided as active ingredients of the compositions useful in the treatment of cancer and diseases associated with multidrug resistance.

6 Claims, 29 Drawing Sheets

| Compound | R1 | R2 | R3 | R4 | R5 | Reference |
|---|---|---|---|---|---|---|
| A | Phe | Leu | ᴅLeu | Val | Leu | Belofsky et al. (1999) |
| 5 | (Br)Phe | NMeLeu | Leu | Val | Leu | Liu et al. (2005) |
| 7 | (Br)Phe | Leu | NMeLeu | Val | Leu | Liu et al. (2005) |
| 11 | (Br)Phe | Leu | Leu | Val | NMeLeu | Liu et al. (2005) |
| 26 | Phe | Leu | Leu | Val | ᴅVal | Styers et al. (2006) |
| 27 | Phe | Leu | Leu | ᴅVal | Leu | Styers et al. (2006) |
| 32 | Phe | Leu | Leu | NMeᴅVal | Leu | Styers et al. (2006) |
| 33 | Phe | Leu | Leu | Val | NMeᴅLeu | Styers et al. (2006) |
| 35 | Phe | ᴅLeu | NMeLeu | Val | Leu | Styers et al. (2006) |

FIG. 6

| | | |
|---|---|---|
| SEQ ID NO: 4 *Solani* | AGTATTCTGGCGGGCATGCCTGTTCGAGCGTCATTACAACCCTCAGGCCCCCGGGCCTGG | 60 |
| SEQ ID NO: 3 Sample | ------------------------------------------------------------GGGCCTGG | 8 |
| SEQ ID NO: 4 *Solani* | CGTTGGGGATCGGCGGAGCCCCCGTGGGCACACGCCGTCCCCAAATACAGTGGCGGTC | 120 |
| SEQ ID NO: 3 Sample | CGTTGGGGATCGGCGGAGCCCCCTGTGGGCACACGCCGTCCCTCAAATACAGTGGCGGTC | 68 |
| SEQ ID NO: 4 *Solani* | CCGCCGCAGCTTCCATCGCGTAGTAGCTAACACCTCGCGACTGGAGAGCGGCGCGGCCAC | 180 |
| SEQ ID NO: 3 Sample | CCGCCGCAGCTTCCATTGCGTAGTAGCTAACACCTCGCAACTGGAGAGCGGCGCGGCCAT | 128 |
| SEQ ID NO: 4 *Solani* | GCCGTAAAACACCCAACTCTTCTGAA-GTTGACCTCGAATCAGGTAGGAATACCCGCTGA | 239 |
| SEQ ID NO: 3 Sample | GCCGTAAAACACCCAACT--TCTGAATGTTGACCTCGAATCAGGTAGGAATACCCGCTGA | 186 |
| SEQ ID NO: 4 *Solani* | ACTTAAGCATATCAATAAGCGGAGGAAAAGAAACCAACAGGGATTGCCCCAGTAACGGCG | 299 |
| SEQ ID NO: 3 Sample | ACTTAAGCATATCAATAAGCGGAGGAAAAGAAACCAACAGGGATTGCCCCAGTAACGGCG | 246 |
| SEQ ID NO: 4 *Solani* | AGTGAAGCGGCAACAGCTCAAATTTGAAATCTGGCTCTCGGGCCCGAGTTGTAATTTGT | 358 |
| SEQ ID NO: 3 Sample | AGTGAAGCGGCAACAGCTCAAATTTGAAATCTGGCTCTCGGGCCCGAGTTGTAATTTGT | 305 |

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Fusarium specific primer P28SL

<400> SEQUENCE: 1
acaaattaca actcgggccc gaga                                          24

<210> SEQ ID NO 2
<211> LENGTH: 23
<212> TYPE: DNA
<213> ORGANISM: Artificial Sequence
<220> FEATURE:
<223> OTHER INFORMATION: Fusarium specific primer P58SL

<400> SEQUENCE: 2
agtattctgg cgggcatgcc tgt                                           23

<210> SEQ ID NO 3
<211> LENGTH: 305
<212> TYPE: DNA
<213> ORGANISM: Fusarium solani

<400> SEQUENCE: 3
gggcctggcg ttggggatcg gcggagcccc ctgtgggcac acgccgtccc tcaaatacag   60
tggcggtccc gccgcagctt ccattgcgta gtagctaaca cctcgcaact ggagagcggc  120
gcggccatgc cgtaaaacac ccaacttctg aatgttgacc tcgaatcagg taggaatacc  180
cgctgaactt aagcatatca ataagcggag gaaaagaaac caacagggat tgccccagta  240
acggcgagtg aagcggcaac agctcaaatt tgaaatctgg ctctcgggcc cgagttgtaa  300
tttgt                                                              305

<210> SEQ ID NO 4
<211> LENGTH: 358
<212> TYPE: DNA
<213> ORGANISM: Fusarium solani

<400> SEQUENCE: 4
agtattctgg cgggcatgcc tgttcgagcg tcattacaac cctcaggccc ccgggcctgg   60
cgttggggat cggcggagcc ccccgtgggc acacgccgtc ccccaaatac agtggcggtc  120
ccgccgcagc ttccatcgcg tagtagctaa cacctcgcaa ctggagagcg gcgcggccac  180
gccgtaaaac acccaactct ctgaagttg acctcgaatc aggtaggaat acccgctgaa  240
cttaagcata tcaataagcg gaggaaaaga aaccaacagg gattgcccca gtaacggcga  300
gtgaagcggc aacagctcaa atttgaaatc tggctctcgg gcccgagttg taatttgt    358

CYCLIC PENTADEPSIPEPTIDES AND MICROORGANISM OF *FUSARIUM* STRAIN PRODUCING THE SAME

CROSS-REFERENCE TO RELATED APPLICATION

This application is a continuation of U.S. Application of Ser. No. 12/600,830 filed on May 10, 2011, which is a U.S. national phase application, pursuant to 35 U.S.C. §371, of PCT/KR2009/000005 filed Jan. 2, 2009. The entire contents of the aforementioned patent applications are incorporated herein by this reference.

SEQUENCE LISTING

The instant application contains a Sequence Listing which has been submitted in ASCII format via EFS-Web and is hereby incorporated by reference in its entirety. Said ASCII copy, created on Sep. 17, 2013, is named 85180_302469_ST25.txt and is 4,096 bytes in size.

TECHNICAL FIELD

The present invention relates to medicinally useful compounds and a microorganism producing the same. More particularly, the present invention relates to novel cyclic pentadepsipeptides with excellent multidrug resistance-reversing activity and inhibitory activity against cancer cells, which are produced by a soil stain of the genus *Fusarium*.

BACKGROUND ART

A fungus of the genus *Fusarium* distributed in association with higher marine plants has proven to be a promising source for the production of sansalvamide, a kind of cytotoxic cyclic depsipeptide.

Sansalvamide A was first reported to be produced by *Halodule wrightii*, a kind of marine microorganisms [Belofsky G N, Jensen P R, Fenical W. (1999) Sansalvamide: A new cytotoxic cyclic depsipeptide produced by a marine fungus of the genus *Fusarium*. *Tetrahedron Lett*. 40, 2913-2916]. It is composed of four hydrophobic amino acid residues (phenylalanine, two leucines, valine) and one hydroxy acid ((S)-2-hydroxy-4-methylpentanoic acid; O-Leu) with five stereogenic centers all having S-stereochemistry. Sansalvamide A was found to have marked anti-proliferative effects on 60 cell lines of the National Cancer Institute, with inhibitory activity against topoisomerase I. Anti-cancer effects of Sansalvamide A may be, at least in part, mediated by this mechanism. Further, the analogues formed by N-methylation or para-bromination of sansalvamide A of FIG. 1 were also found to exhibit remarkable cytotoxicity against human pancreatic cancer cells, suggesting that these cyclic compounds may be highly useful as anti-cancer agents [Ujiki M B, Milam B, Ding X Z, Roginsky A B, Salabat M R, Talamonti M S, Bell R H, Gu W, Silverman R B, Adrian T E. (2006) A novel peptide sansalvamide analogue inhibits pancreatic cancer cell growth through G0/G1 cell-cycle arrest. *Biochem. Bioph. Res. Co*. 340, 1224-1228].

Recently, N-methylsansalvamide, a sansalvamide analogue with N-methylation, has been produced from different *Fusarium* species isolated from green algae. It consists of four amino acid residues (phenylalanine, leucine, N-methylleucine and valine) and one hydroxy acid (O-Leu). N-Methylsansalvamide was reported to exhibit in vitro cytotoxicity in the NCI human tumor cell line screen [Cueto M, Jensen P R, Fenical W. (2000) N-Methylsansalvamide, a cytotoxic cyclic depsipeptide from a marine fungus of the genus *Fusarium*. *Phytochemisuy*, 55, 223-226].

Multidrug resistance (MDR) is arising as one of the major obstacles to successful chemotherapy for human cancer. A variety of biochemical, pharmacological and clinical strategies for overcoming MDR have been designed and suggested [Teodori E, Dei S, Scapecchi S, Gualtieri F. (2002) The medicinal chemistry of multidrug resistance (MDR) reversing drugs. *II Farmaco* 57, 385-415]. Although there are several mechanisms associated with MDR, the overexpression of P-glycoproteins (P-gp) and multidrug resistance-associated proteins (MRP) is known to be responsible for the development of MDR in cancer cells [Thomas H, Coley H M. (2003) Overcoming multidrug resistance in cancer: an update on the clinical strategy of inhibiting P-glycoprotein. *Cancer Control* 10, 159-165; Perez-Tomas R. (2006) Multidrug resistance: retrospect and prospects in anti-cancer drug treatment. *Curr. Med. Chem*. 13, 1859-1876].

Sansalvamide A is a lipophilic, cyclic depsipeptide, which is of protease resistance and membrane permeability, so that it may advantageously take an oral route, compared to other drugs. In addition, forming a cyclic core structure, composed of four amino acids and one hydroxy acid, in which rotation around C—C bonds is restricted, sansalvamide A has a firm conformation which is of excellent compatibility to the body and enjoys a long half life.

Although there have been a number of sansalvamide analogues synthesized to utilize the structural merits and the cytotoxicity against cancer cells of sansalvamide A or N-methylsansalvamide, none of them are concerned with separated, cyclic pentadepsipeptides.

SUMMARY

It is therefore an object of the present invention to provide a strain of the genus *Fusarium* producing novel cyclic pentadepsipeptides.

It is another object of the present invention to provide a method of producing the novel cyclic pentadepsipeptides by culturing a strain of the genus *Fusarium*.

It is a further object of the present invention to provide novel cyclic pentadepsipeptides.

It is a still further object of the present invention to provide a pharmaceutical composition for reversing multidrug resistance.

It is still another object of the present invention to provide a pharmaceutical composition for the treatment of cancer.

In accordance with an aspect thereof, the present invention pertains to a novel cyclic peptadepsipeptide represented by Chemical Formula 1 or 2:

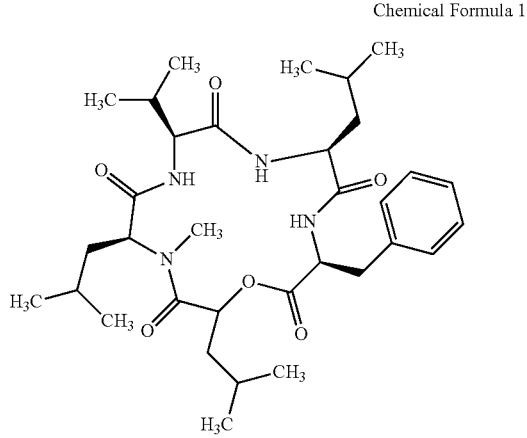 [SMILES: CC(C)CC1OC(=O)[C@H](Cc2ccccc2)NC(=O)[C@H](CC(C)C)NC(=O)[C@H](C(C)C)NC(=O)[C@H](CC(C)C)N(C)C1=O]

Chemical Formula 1

Chemical Formula 2

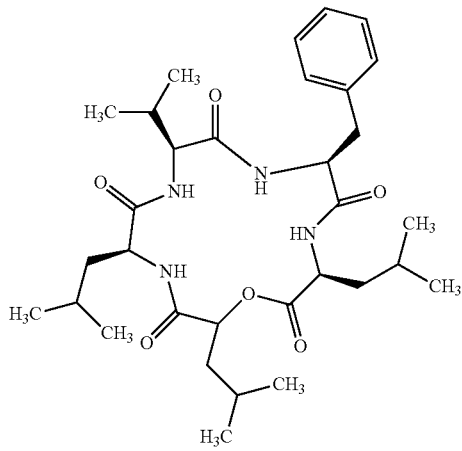

BRIEF DESCRIPTION OF DRAWINGS

FIG. 6 shows an array of ITS-5.8 rDNA sequences of the strain of the present invention (sample; SEQ ID NO: 3) and Fusarium solani (SEQ ID NO: 4) for homology comparison therebetween.

DETAILED DESCRIPTION

Figure 1:
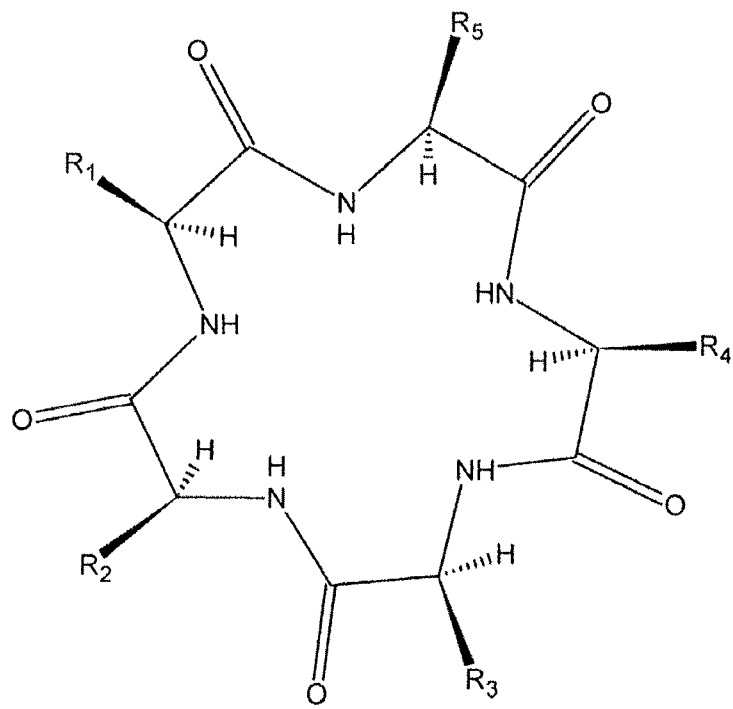
FIG. 1 shows the chemical structure of sansalvamide A analogues.
Figure 2:
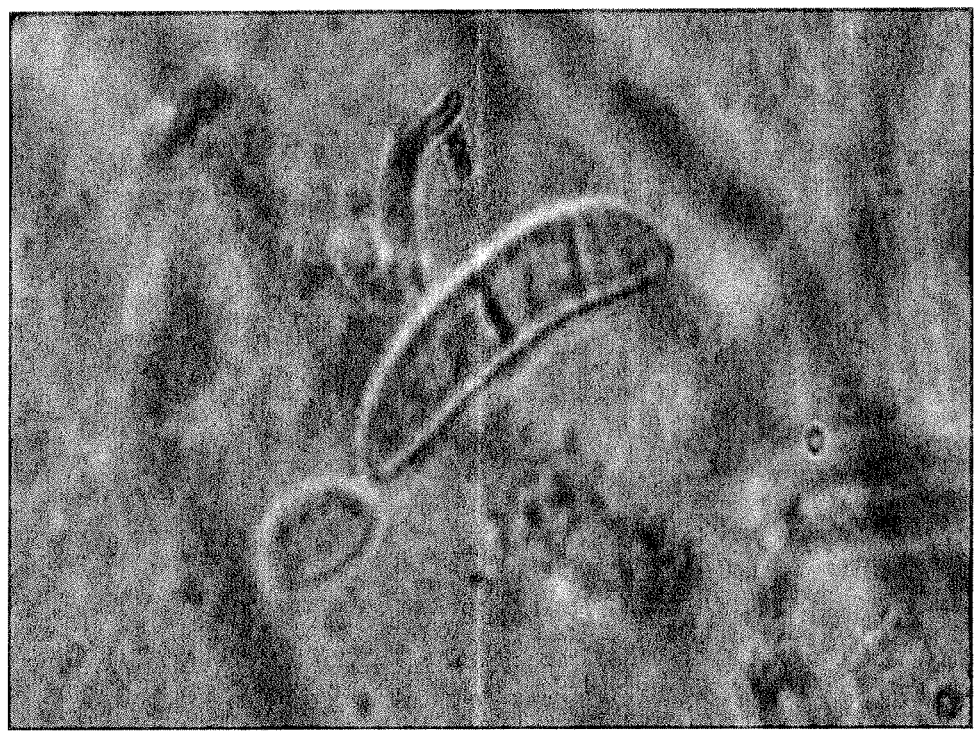
FIG. 2 is a photograph showing microconidia of the strain of the present invention.
Figure 3:
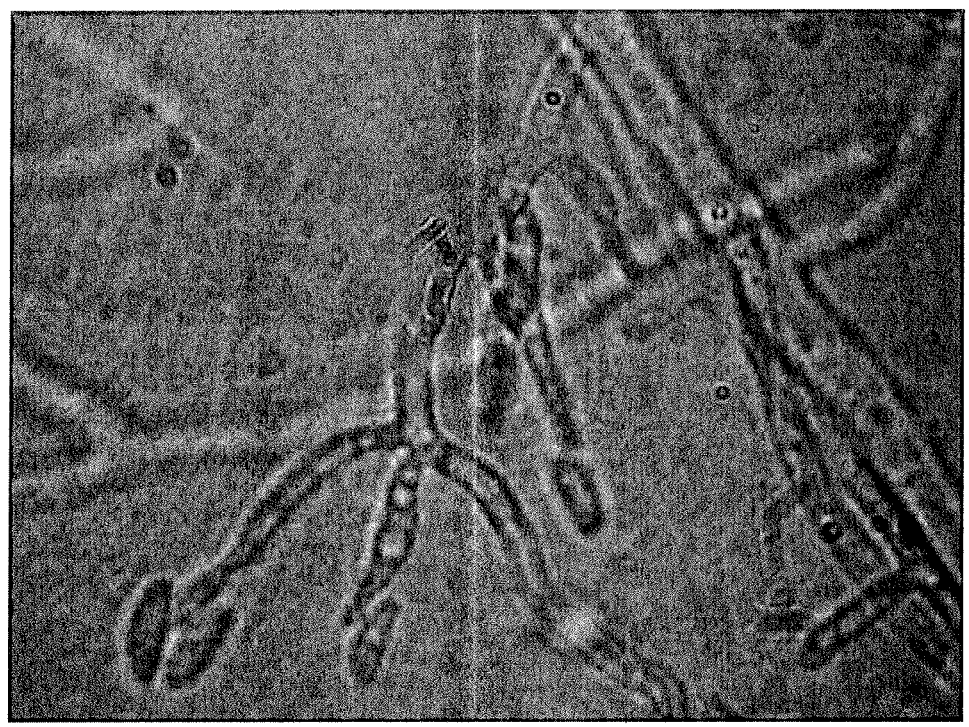
FIG. 3 is a photograph showing the conidiophores of the Fusarium strain according to the present invention.
Figure 4:
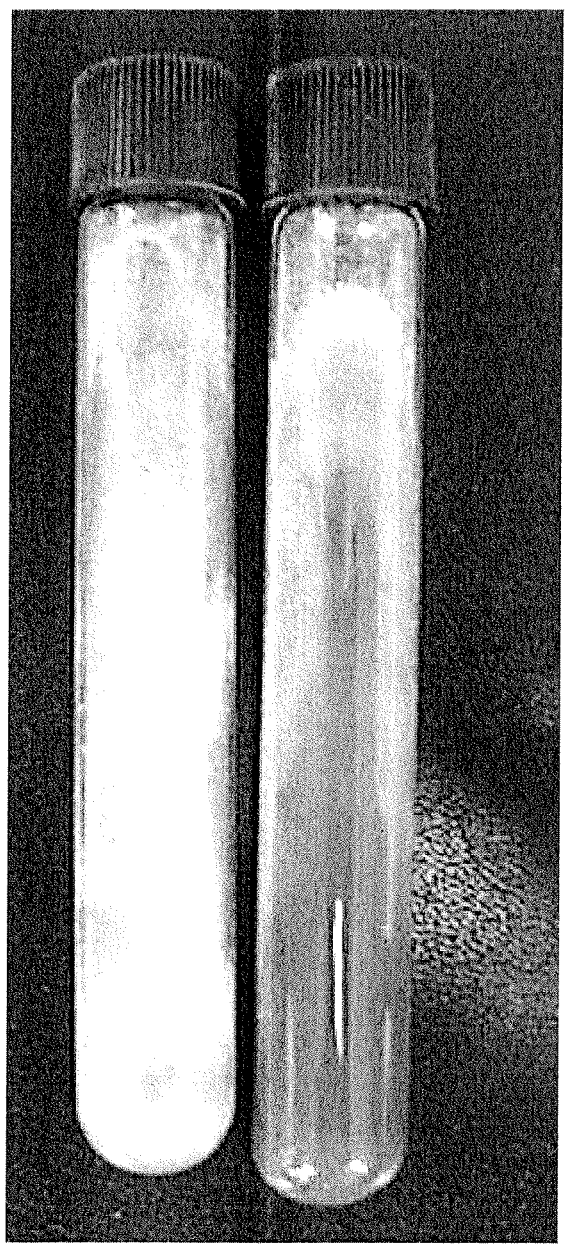
FIG. 4 is a photograph showing the appearances of the surface and backside of an agar on which the strain of the present invention is grown.
Figure 5:
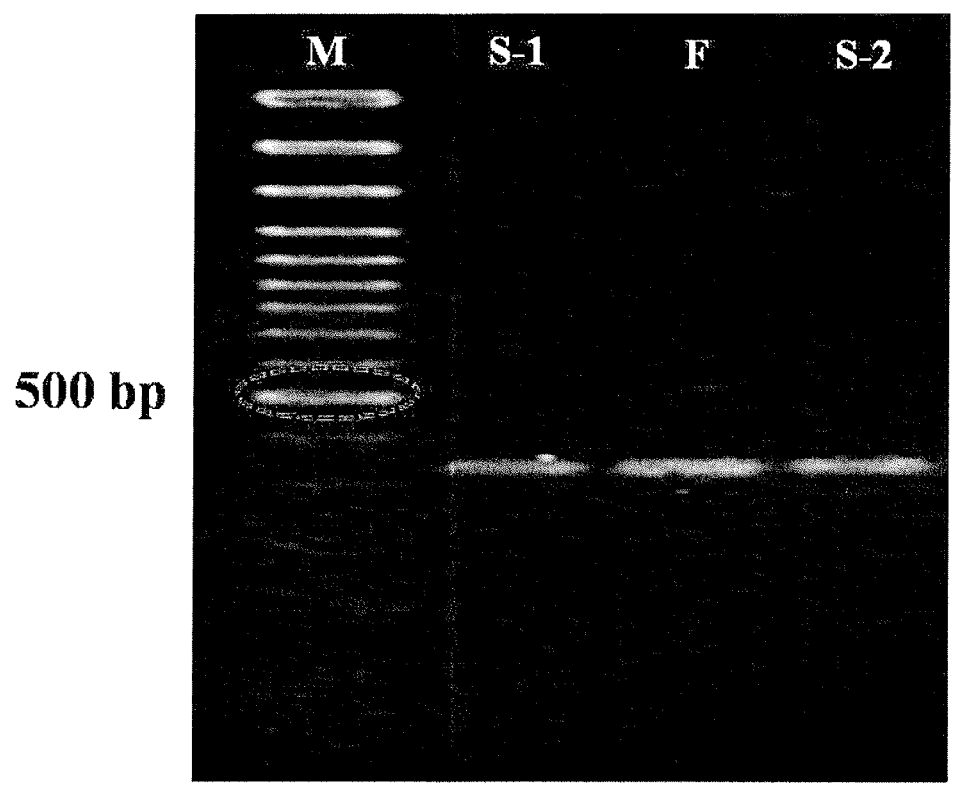
FIG. 5 is a photograph showing PCR products amplified from DNA templates of Fusarium strain (M, 100-bp DNA ladder; F, Fusarium strain; S-1, Fusarium moniliforme NRRL 13569; S-2, Fusarium oxysporum KCCT 16909).

The cyclic pentadepsipeptides, represented by Chemical Formulas 1 and 2, according to the present invention are 15-membered ring compounds which are proven novel with a difference from conventionally reported sansalvamide A and N-methylsansalvamide in the sequence of their constitutional amino acids and hydroxy acid. As seen in FIG. 1, conventional analogues synthesized on the basis of the core structure of sansalvamide A are intended to increase in cytotoxicity as a result of the bromination of the benzene ring of phenyl alanine or the methylation of leucine or valine. Nowhere has an attempt to change the sequence of the constitutional amino acids and hydroxy acid of sansalvamide A or N-methylsansalvamide been mentioned in previous reports. Further, organic synthesis for altering the sequence of the constitutional amino acids and hydroxy acid is accompanied by the interruption of the ester bond between the hydroxy acid ((S)-2-hydroxy-4-methylpentanoic acid; OLeu) and the phenylalanine within the core structure.

Being different from sansalvamide A and N-methylsansalvamide in the sequence of the constitutional four amino acids and one hydroxy acid, the novel, cyclic pentadepsipeptides, represented by Chemical Formulas 1 and 2, according to the present invention have cytotoxicity over a wide spectrum of types of cancer that is as potent as that of sansalvamide A. Furthermore, the cyclic pentadepsipeptides of Chemical Formulas 1 and 2 show the drug resistance-reversing activity which has not yet been reported in conventional analogues synthesized on the basis of the sansalvamide A or N-methylsansalvamide. Excellent drug resistance-reversing activity is found in the cyclic pentadepsipeptide of Chemical Formula 1. When pathogens or cells are exposed to chemotherapy, they may become resistant to the drug and possibly to other structurally unrelated drugs. The pathogens or cells are said to be drug-resistant when drugs meant to neutralize them have a reduced effect. As used herein, the term "drug resistance-reversing activity" is intended to mean not only suppressing the generation of drug-resistant cells or keeping the cells sensitive to the drugs, but also increasing or recuperating the sensitivity of drug-resistant cells to the drugs.

Having the ability to make drug-resistant cells sensitive to drugs or suppress the generation of drug-resistant cells, the cyclic pentadepsipeptides of Chemical Formulas 1 and 2 according to the present invention or pharmaceutically acceptable salts thereof may be useful in the treatment of multidrug-resistant cancer.

Preferably, the cyclic pentadepsipeptides of Chemical Formulas 1 and 2 or pharmaceutically acceptable salts thereof may be used in combination with conventional drug-resistant inhibitors such as cyclosporine or analogues, phenothiazine, thioxantheres, verapamil, etc.

Also, the cyclic pentadepsipeptides of Chemical Formulas 1 and 2 according to the present invention or pharmaceutically acceptable salts thereof may be used in combination with anticancer agents, that is, standard chemotherapy agents, in the treatment of cancer and preferably in the treatment of tumors resistant to drugs a priori or a posteriori.

In accordance with another aspect thereof, the present invention pertains to a *Fusarium* strain producing the cyclic pentadepsipeptide of Chemical Formula 1 or 2. Preferably, the *Fusarium* strain producing the novel compound is *Fusarium solani* KCCM90040 [Accession No.: KCCM10881P].

In accordance with a further aspect thereof, the present invention pertains to a method for producing the cyclic pentadepsipeptide of Chemical Formula 1 or 2 by culturing the strain. This culturing is preferably conducted on a cereal substance. The cereal substance useful in the present invention is selected from among rice, wheat, maize, rye, Indian millet, barley and a combination thereof, preferably from among rice, wheat, maize and rye, more preferably from among rice and wheat, and most preferably rice.

When cultured in a seawater-based medium, marine *Fusarium* strains were reported to produce sansalvamide in an amount of 0.642 g per 17 liters [Belofsky G N, Jensen P R, Fenical W. (1999) Sansalvamide: A new cytotoxic cyclic depsipeptide produced by a marine fungus of the genus *Fusarium. Tetrahedron Lett.* 40, 2913-2916]. As for the *Fusarium* strain CNL-619, its N-methylsansalvamide production was reportedly 3.1 mg/L in a seawater-based medium [Cueto M, Jensen P R, Fenical W. (2000) N-Methylsansalvamide, a cytotoxic cyclic depsipeptide from a marine fungus of the genus *Fusarium. Phytochemistry.* 55, 223-226].

Being produced from the marine *Fusarium* strains, sansalvamide or N-methylsansalvamide requires a seawater-based medium for the production thereof. Further, the marine strains are very poor in the productivity of sansalvamide or N-methylsansalvamide per volume of medium. In contrast, the *Fusarium* strain of the present invention is of soil origin and can produce the compound of Chemical Formula 1 or 2 in high yield on a solid cereal substance.

The cereal substance useful for culturing the strain is preferably rice. In order to produce the compound of Chemical Formula 1 or 2, the strain of the present invention is preferably cultured at a temperature of from 20 to 30° C. and at an RH of from 20 to 50% for 10~20 days. Optimally, it is cultured at 25.84° C. and 37.99% RH for 16.03 days.

A strain producing a cyclic depsipeptide was isolated from potatoes grown in Munkyoung Korea and identified as a strain of *Fusarium solani*. It was named *Fusarium solani* KCCM90040 and deposited with the Korean Culture Center of Microorganisms on Jan. 15, 2008 with accession No. KCCM10881P according to the Budapest Treaty.

The compounds of produced by the strain were analyzed to be 15-membered ring compounds different from sansalvamide A and N-methylsansalvamide in the sequence of constitutional amino acids and hydroxy acid and identified as cyclic pentadepsipeptides of Chemical Formulas 1 and 2.

The cyclic pentadepsipeptides of Chemical Formula 1 or 2 in accordance with the present invention or pharmaceutically acceptable salts thereof shows inhibitory activity against drug-resistant cells, which may be tumor cells or antibiotic-resistant cells, and thus can be used as an active ingredient of a pharmaceutical composition for inhibiting the drug resistance of cells.

Thanks to their suppressive activity against tumor proliferation, the pentadepsipeptides of Chemical Formula 1 and 2 in accordance with the present invention may also be used as an active ingredient of a pharmaceutical composition for the treatment of cancer.

The term "pharmaceutically acceptable salt", as used herein, means non-toxic organic or inorganic acid addition salts of the compounds of interest. Examples of the inorganic acids useful in the present invention include hydrochloric acid, hydrobromic acid, sulfuric acid, acid metal salts (e.g., sodium hydrogen phosphate, potassium hydrogen sulfate), etc. Examples of the organic acid useful in the present invention include mono-, di- and tricarboxylic acid. Among the pharmaceutically acceptable acids, there may be mentioned, without implying any limitation, acetic acid, glycolic acid, lactic acid, pyruvic acid, malonic acid, succinic acid, glutaric acid, fumaric acid, malic acid, tartaric acid, citric acid, ascorbic acid, maleic acid, hydroxymaleic acid, benzoic acid, hydroxybenzoic acid, phenylacetic acid, cinnamic acid, salicylic acid and 2-phenoxybenzoic acid. Other organic acids may be exemplified by methane sulfonic acid and 2-hydroxyethane sulfonic acid. Such salts can be either in hydrated or anhydrous form. The acid addition salts of these compounds are prepared using a typical method, for example, by dissolving a free base in a suitable solvent such as an aqueous solvent, an alcohol solvent or another acid-containing solvent, and then evaporating the solvent, or by reacting the free base with the organic solvent (in this case, the salt may be directly separated or obtained via concentration). Generally, the acid addition salts of the compounds of the present invention are crystalline materials which can be dissolved in water or various hydrophilic organic solvents and generally display higher melting points compared to the free base forms thereof.

The pharmaceutical compositions of the present invention for the treatment of cancer or diseases associated with multidrug resistance may be administered to subjects in need thereof. As used herein, the term "subject" is intended to include mammals such as goats, horses, cow, pigs, dogs, cats, mice, rats, etc. as well as primates such as humans.

The effective dosages of the cyclic pentadepsipeptides of Chemical Formulas 1 and 2 or pharmaceutically acceptable salts thereof may vary depending on various factors including dosage units, the duration of treatment, the age and sex of the patient, traits of the tumor to be treated, drug resistance, etc.

In combination with other anticancer agents, particularly chemical agents useful for the treatment of tumors, the cyclic pentadepsipeptides of Chemical Formulas 1 and 2 or pharmaceutically acceptable salts thereof may be used. For reversing multidrug resistance, the cyclic pentadepsipeptides of Chemical Formulas 1 and 2 or pharmaceutically acceptable salts thereof may be administered at an effective dose of from 15 mg/kg to 500 mg/kg. A unit daily dosage may contain 25 to 500 mg of the cyclic pentadepsipeptide of Chemical Formula 1 or 2 or a pharmaceutically acceptable salt thereof. The cyclic pentadepsipeptides of Chemical Formulas 1 and 2 or pharmaceutically acceptable salts thereof may be in an oral or parenteral dosage form formulated with a pharmaceutically acceptable carrier.

For use in the treatment of tumors, the cyclic pentadepsipeptides of Chemical Formulas 1 and 2 or pharmaceutically acceptable salts thereof are preferably administered at an effective dose, in combination with an anticancer agent, particularly, an agent for chemotherapy.

Among the tumors which can be treated with the compounds of the present invention are benign or malignant tumors, neoplasms, melanoma, lymphoma, leukemia and sarcoma. Examples of the tumors include skin tumors (e.g., malignant melanoma and cutaneous mycosis fungoides), blood tumors (e.g, acute lymphocytic leukemia, acute or chronic myelogenous leukemia), lymphoma (e.g. Hodgkin's disease, malignant lymphoma), gynecologic tumors (ovarian tumor, uterine tumor), urologic tumors (prostate tumor, bladder tumor, seminoma), soft tissue sarcoma, osteo- or non-osteosarcoma, breast tumors, pituitary tumors, thyroid gland tumors, adrenal cortex tumors, gastrointestinal tumors (esophagus tumor, stomach tumors, intestine tumor, and colon tumor), pancreatic tumors, liver tumors, larynx tumors, papilloma and lung tumors. The best therapeutic effects may be elicited when the compounds of the present invention are applied to multidrug-resistant tumors or tumors which become multidrug resistant. Among these tumors are colon tumors, lung tumors, stomach tumors and liver tumors.

A cytotoxic agent is typical of the chemical agents which can be applied together with the cyclic pentadepsipeptides of Chemical Formulas 1 and 2 or pharmaceutically acceptable salts thereof. Examples of the agents for chemotherapy include cyclophosphamide, methotrexate, prednisone, 6-mercaptopurine, procarbazine, daunorubicin, vincristine, vinblastine, chlorambucil, cytosine arabinoside, 6-thioguanine, thio TEPA, 5-fluorouracil, 5-fluoro-2-deoxyuridine, 5-azacytidine, nitrogen mustard, 1,3-bis(2-chloroethyl)-1-nitrosourea (BCNU), (1-(2-chloroethyl)-3-cyclohexyl-1-nitrosourea) (CCNU), busulfan, adriamycin, bleomycin, vindesine, Cycloleucine and methylglyoxal bis(guanyl hydrazone) (MGBG).

The effective dosage of the chemical agent useful in the present invention may vary depending on various factors including the condition of the patient, the morphology and size of the tumor, kind of the agents, etc, and may be readily determined by those skilled in the art. Generally, the chemical agent may be administered in a smaller dose when administered in combination with the cyclic pentadepsipeptides of Chemical Formulas 1 and 2 or pharmaceutically acceptable salts thereof than when administered alone. The reason is because a large amount of the chemical agent may cause drug resistance. Also, a cocktail of chemical agents or surgery or radiotherapy may be used, together with the administration of the cyclic pentadepsipeptides of Chemical Formulas 1 and 2 or pharmaceutically acceptable salts thereof. Although the co-administration of the cyclic pentadepsipeptides of Chemical Formulas 1 and 2 or pharmaceutically acceptable salts thereof and the chemical agent is described above, they may not be in the same dosage form or may not be administered at the same time. Accordingly, the cyclic pentadepsipeptides of Chemical Formulas 1 and 2 or pharmaceutically acceptable salts thereof and the chemical agent may be administered in a mixture or at different times.

An oral route is preferable. For use in oral administration, the cyclic pentadepsipeptides of Chemical Formulas 1 and 2 or pharmaceutically acceptable salts thereof may be formulated into solid or liquid forms, such as capsules, pills, tablets, troches, lozenge, melts, powders, liquids, suspensions and emulsions. Typical of the solid dosage forms is a capsule. A capsule with a soft or hard gelatin envelope may contain a surfactant, a lubricant, and an inert filler such as lactose, sucrose, calcium phosphate and corn starch. In another embodiment, the compounds of the present invention may be formulated into a tablet, together with a tablet base (e.g., lactose, sucrose, corn starch), a binder (e.g, acacia, corn starch or gelatin), a disintegrant (e.g., potato starch, alginic acid, corn starch and guar gum) for facilitating the degradation and dissolution of the tablet after administration, a lubricant (e.g., talc, stearic acid or magnesium stearate, calcium stearate or zinc stearate) for enhancing the release of tablet granules and preventing the attachment of the tablet drug to the tabletting die or punch, and a dye, a colorant and a fragrant for improving the color and taste of the tablet. Carriers suitable for use in oral liquid dosage forms include suspension agents, water mixed with or without an emulsifier, and a diluent such as an alcohol (ethanol, benzyl alcohol and polyethylene alcohol).

Also, the cyclic pentadepsipeptides of Chemical Formulas 1 and 2 or pharmaceutically acceptable salts thereof may be administered in the form of a solution in a diluent, together with a pharmaceutically acceptable carrier, through a parenteral route, that is, a subcutaneous, intravenous, intramuscular or intraperitoneal route. Examples of the carrier for use in injection include pharmaceutically acceptable surfactants (e.g., soap or detergent), suspending agents (pectin, carbomer, methylcellulose, hydroxypropylmethylcellulose or carboxymethylcellulose), water or saline mixed with an emulsifier or another pharmaceutical adjuvant, aqueous solutions of dextrose or corresponding sugars, alcohols (e.g., ethanol, isopropanol, hexadecylalcohol), glycol (e.g., propylene glycol, or polyethylene glycol), glycerol ketal (e.g., 2,2-dimethyl-1,3-dioxolan-4-methanol), ethers (e.g., poly(ethylene-glycol)400), oils, and germ-free solutions or mixture containing fatty acids, fatty acid esters or glycerides, or acetylated fatty acid glycerides. Examples of the oil useful in the formulation of parenteral dosage forms include petroleum, animal oil, vegetable oil, or synthetic oil, such as peanut oil, soybean oil, sesame oil, cotton seed oil, corn oil, olive oil, mineral oil and inorganic oil. Among the fatty acids are oleic acid, stearic acid and isostearic acid. The fatty acid esters may be exemplified by oleic acid ethyl and myristic acid isopropyl. Alkaline metal salts, ammonium salt and triethanolamine salts of fatty acids may be suitable as the surfactant. Examples of the detergent include cationic detergents (e.g., dimethyl dialkyl ammonium halide, alkyl pyridium halide and alkylamine acetate), anionic detergents (e.g., alkyl, aryl and olefin sulfonate, alkyl, olefin, ether and monoglyceride sulfate and sulfosuccinate), non-ionic detergents (lipid amine oxide, fatty acid alkanolamide and polyoxyethylenepolypropylene copolymer), and amphiphatic detergents (e.g., alkyl-β-amino propionate and 2-alkylimidazolin quarternary ammonium salt) and a combination thereof. Typically, the parenteral compositions of this invention will contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

In accordance with a further aspect thereof, the present invention pertains to a method of producing the cyclic pentadepsipeptide of Chemical Formula 1 or 2 by culturing a strain of the genus *Fusarium*, preferably *Fusarium solani*, more preferably *Fusarium solani* KCCM90040 [accession No.: KCCM10881P]. Alternatively, the compound of the present invention may be prepared through biosynthesis or organic synthesis.

EXAMPLES

A better understanding of the present invention may be obtained through the following examples which are set forth to illustrate, but are not to be construed as limiting the present invention.

Example 1

Isolation and Identification of *Fusarium* Strain (1) Isolation and Morphological Identification

*Fusarium* strains were isolated from *Fusarium*-contaminated potatoes in Munkyeong, Korea and its identification was determined using the methods of Samson, et al. and the method of Nelson et al. [Samson R A, Hoekstra E S, Oorschot V, Connie A N. (1981) Introduction to food-borne fungi. Published and distributed by Centraalbureau voor Schimmelcultures; Nelson P E, Toussoun T A, Marasas W F. (1983) *Fusarium* species: An illustrated manual for identification. The Pennsylvania State University Press].

The isolated *Fusarium* strain was transferred on carnation leaf agar (CLA) and real potato dextrose agar (RPDA) and analyzed for morphological characteristics.

The microconidia were present in abundance generally in the form of single cells of an oval to kidney shape (FIG. 2). Conidiophores of the *Fusarium* strain put out branches as shown FIG. 3. The microconidia and conidiophores of *F. solani* are morphologically similar to those of *Fusarium oxysporum*. The microconidia of *F. oxysporum* were observed to be larger in size and have thicker walls and conidiophores were formed on short monophialides, compared to those of *F. solani* (Nelson et al., 1983). The isolated *Fusarium* strains grew fast. The slant surface of the agar was almost covered with white mycelia with the back being a dark cream (FIG. 4).

From these morphological characteristics, the *Fusarium* strain was identified as *F. solani.*

(2) Molecular Biological Identification

A. DNA Isolation

The total genomic DNA of the isolated *Fusarium* strain was extracted from the mycelia grown on PDA (potato dextrose agar) using the method of Correll [Correll J C, Klittich C J R, Leslie J F. (1987) Nitrate nonutilizing mutants of *Fusarium oxysporum* and their use in vegetative compatibility tests. *Phytopathology,* 77, 16401646].

In this regard, mycelium-covered agar was placed in a tube filled with liquid nitrogen, followed by evaporating the liquid nitrogen at room temperature. This procedure of liquid nitrogen filling and evaporation was repeated again. After evaporation of the liquid nitrogen, 0.5 mL of a lysis buffer [50 mM Tris pH 8.0, 50 mM ethylenediaminetetraacetic acid (EDTA), 3% sodium dodecylsulfate (SDS), 1% 2-mercaptoethanol and 0.1 m/ml proteinase K] warmed to 65° C. was added into the tube and incubated for 1 hr at 65° C. After incubation, 0.5 mL of a phenol solution was added and then spun for 5 min at 8,000 rpm in a microcentrifuge to separate a phenol phase and an aqueous phase from each other. The aqueous phase was transferred to a new tube. The phenol extraction was repeated again. Phenol residues in the aqueous phase were removed with 0.4 mL of a mixture of chloroform:isoamyl alcohol (24:1). Ammonium acetate (0.05 ml, 7.5 M) was mixed gently with the aqueous phase. DNA was precipitated with 0.88 mL of 95% ethanol cold to −20° C. The DNA pellet was spun down for 20 min at 13,000 rpm. The pellet was rinsed with 70% ethanol, spun down, and dried. The DNA was resuspended in TE buffer (10 mM Tris, 1 mM EDTA, pH 8.0) and stored until use.

B. Identification by DNA Electrophoresis and Homology Comparison

*Fusarium* specific primers, P28SL (5'-ACA AAT TAC AAC TCG GGC CCG AGA-3') of SEQ ID NO: 1 and P58SL (5'-AGT NIT CTG GCG GGC ATG CCT GT-3') of SEQ ID NO: 2, designed as described by Hue et al. [Hue, F. X., M. Huerre, M. A. Rouffault, and C. D. Bievre. Specified detection of *Fusarium* species in blood and tissues by a PCR technique. Journal of Clinical Microbiology, 37: 2434-2438. 1999] were used for a control PCR assay. A pair of the *Fusarium* specific primers amplified a fragment of DNA coding for the ribosomal DNA (rDNA) of *Fusarium* strains by PCR. The binding sites of the P28SL and P58SL primers, corresponding to the ITS2 region and a portion of 5.8s and 28s rDNA, are conserved among *Fusarium* strains.

For PCR, 1 ng of the DNA isolated in A was used together with a primer pair of the primers P28SL and P58SL, and a PCR pre-mixture purchased from Promega. Starting by denaturation at 94° C. for 10 min, PCR was performed with 40 cycles of denaturation at 94° C. for 1 min, annealing at 60° C. for 1 min and extension at 72° C. for 1 min, followed by a final extension at 72° C. for 10 min.

The PCR product thus obtained was run on a 2% agarose gel in Tris-acetate-EDTA buffer in the presence of an electric field. After completion of the electrophoresis, the gel was stained with ethidium bromide and visualized under UV light.

The PCR product (F) amplified from *Fusarium* stains was detected at a position between 300 and 400 bp, which matched with the sizes of PCR products from two controls *Fusarium moniliforme* NRRL 13569 and *Fusarium oxysporum* KCTC 16909 (FIG. 5).

The PCR product obtained with the *Fusarium*-specific primers was purified and sequenced commercially (Macrogen Inc. Seoul, Korea). BLAST search for homology in the GenBank database showed that the ITS-5.8 rDNA sequence of the *Fusarium* strain (SEQ ID NO: 3) of the present invention shared more than 98% homology with those of *F. solani*

(FIG. 6; given in SEQ ID NO: 4). The ITS-5.8 rDNA sequence of the *Fusarium* strain is given in SEQ ID NO: 3.

This *Fusarium* strain was named *Fusarium solani* KCCM90040 and deposited with the Korean Culture Center of Microorganisms on Jan. 15, 2008 with accession No. KCCM10881P, according to the Budapest Treaty.

Example 2

Production and Separation of Cyclic Depsipeptide (1) Cultivation in *Fusarium* Defined Medium

*Fusarium solani* KCCM90040 was inoculated at a density of 1×10$^5$ spores/mL into 100 mL of a *Fusarium* defined medium (FDM) broth (25 g of sucrose, 4.25 g of NaNO$_3$, 5 g of NaCl, 2.5 g of MgSO$_4$7H2O, 1.36 g of KH$_2$PO$_4$, 0.01 g of FeSO$_4$7H2O, and 0.0029 g of ZnSO$_4$7H2O per liter) and incubated at 25° C. for 7 days.

(2) Cultivation on Cereal Substrate

*Fusarium solani* KCCM90040 was inoculated at a density of 1×10$^5$ spores/mL to a rice medium which was prepared from 50 g of autoclaved rice with the water content thereof adjusted to 40 wt % with sterile distilled water, followed by culturing at 25° C. for 7 days.

(3) Extraction of Cyclic Depsipeptide from the Culture

To the *Fusarium* strain culture including the mycelia of (1) was added two volumes of chloroform. It was vigorously stirred and the bottom layer was evaporated to dryness. The residue was resuspended in methanol.

The cereal medium in which the *Fusarium* of (2) was cultured was dried at room temperature for 12 hrs. The mycelia thus dried were homogenized, extracted overnight with 75 ml of a solvent mixture of 16:3:1 (v/v/v) acetonitrile:MeOH:water, and filtered through sterile filter paper. The filtrate was defatted twice with 25 mL of n-heptane and the bottom layer was evaporated to dryness. The residue was dissolved in 50 mL of a solvent mixture of 55:45 (v/v) MeOH:water and extracted twice with 25 mL of CH$_2$Cl$_2$. The CH$_2$Cl$_2$ layer was evaporated to dryness, and the residue was resuspended in methanol.

(4) Purification of Cyclic Depsipeptide from the Extracts

Each of the extracts from the cultures of (1) and (2) was flowed for 40 min at a constant flow rate (1 mL/min) along a Shiseido pack C18 column (0.46×25 cm) (Shiseido co., Japan) with a mixture of 70:30 (v/v) acetonitrile:water serving as an eluent. Peaks were read at 210 nm.

Figure 7:
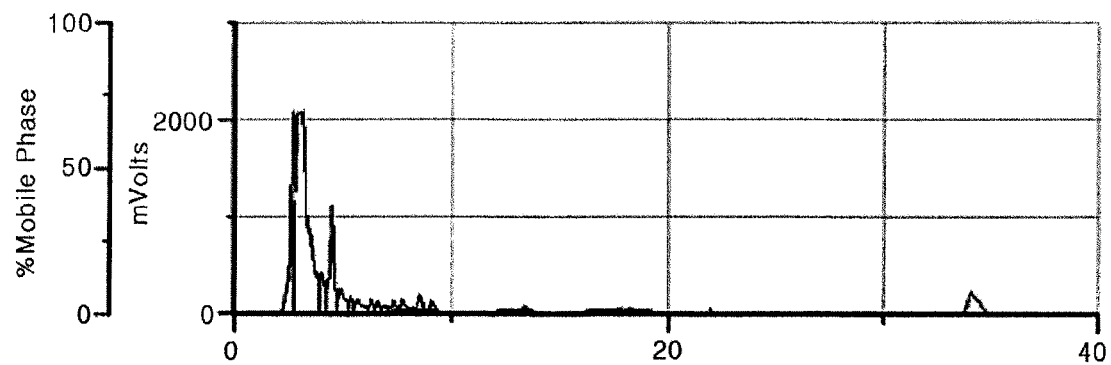
FIG. 7 is an HPLC chromatogram of an extract from a submerged culture of the strain of the present invention after incubation in a Fusarium defined medium.
Figure 8:
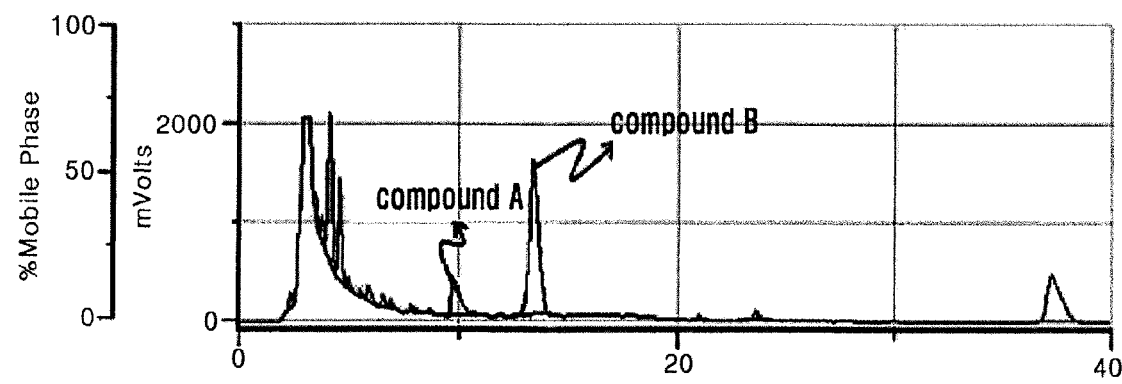
FIG. 8 is an HPLC chromatogram of an extract from a cereal culture of the strain of the present invention after incubation on a cereal culture.

No secondary metabolites were detected in the extract of the culture in FDM of (1) (FIG. 7). On the other hand, two main peaks could be eluted with a retention time of 9.7 and 13.4 minutes from the extract from the culture on the cereal substrate of (2) (FIG. 8). The compounds detected at 9.7 and 13.4 min were named Compound A and B, respectively.

The compounds were separated using a GROM-sil pack ODS preparative column (1.0×25 cm) with a mixture of acetonitrile:water solution (65:35, v/v) serving as a mobile phase at a flow rate of 3 ml/min for 60 min, followed by further purification through a Shiseido pack C18 column (0.46×25 cm) with a mixture of acetonitrile:water (70:30, v/v) at a flow rate of 1 mL/min.

(5) Determination of Molecular Weight

Figure 9:
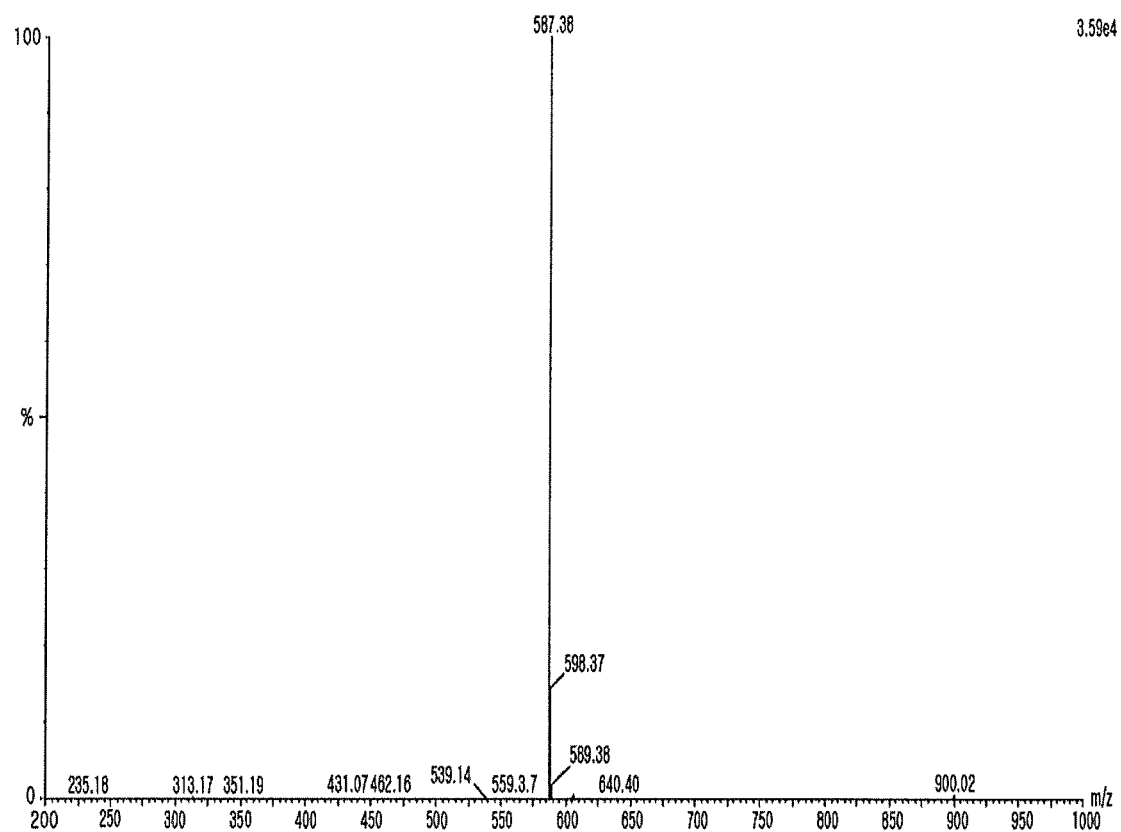
FIG. 9 is of electrospray ionization mass spectra illustrating the molecular weight of Compound A produced by the strain of the present invention.
Figure 10:
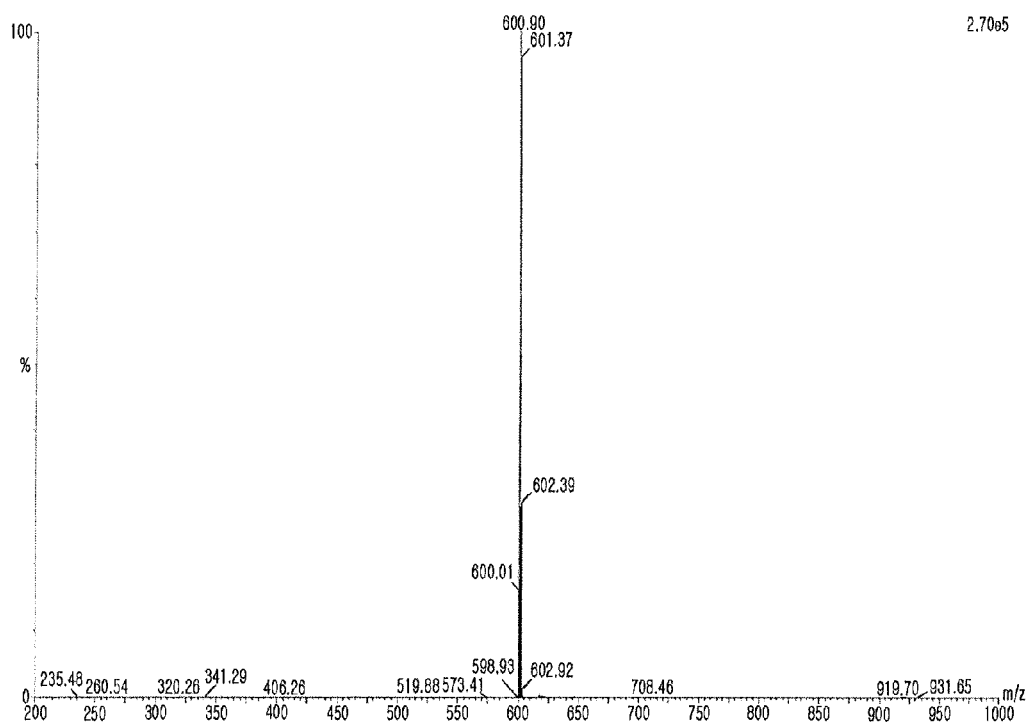
FIG. 10 is of electrospray ionization mass spectra illustrating the molecular weight of Compound B produced by the strain of the present invention.
Figure 11:
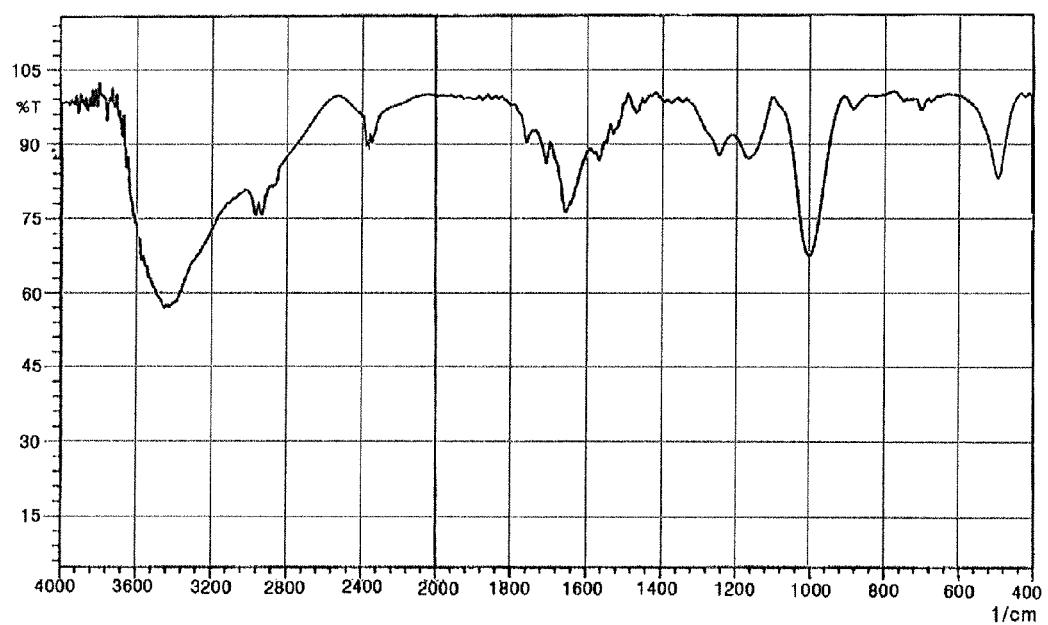
FIG. 11 is of infrared spectra of Compound A, measured by an FT IR-8400S infrared spectrophotometer.

Compounds A and B were found to have molecular weights of 586.36 and 600.36 m/z, respectively, as measured by electrospray ionization mass spectrometry (ESI-MS) (FIGS. 9 and 10).

These mass data of the secondary metabolites (Compounds A and B) were very similar to previously reported ones for cyclic depsipeptides. A summarization of previously reported cyclic depsipeptides for origin, molecular weight, and reference is given in Table 1, below.

TABLE 1

| Cpd. | Mw(m/z) | Origin | Reference |
|---|---|---|---|
| Enniatin H | 653.6 | *F. oxysporum* KFCC1169P | Song et al.[1] |
| Enniatin I | 667.6 | *F. oxysporum* KFCC1169P | Song et al.[1] |
| Enniatin MK1688 | 681.6 | *F. oxysporum* KFCC1169P | Song et al.[1] |
| Sansalvamide | 586 | Marine *Fusarium* sp. | Belofsky[2] |
| N-Methylsansalvamide | 600 | Marine *Fusarium* sp. | Cueto.[3] |
| Zygosporamide | 634.38 | Marine *Fusarium* sp. (*Zygosporium masonii*) | Oh[4] |

[1]Song H H, Ahn J H, Lim Y H, Lee C, (2006) Analysis of beauvericin and unusual enniatins co-produced by *Fusarium oxysporum* FB1501 (KFCC 11363P). *J. Microbiol. Biotechnol.* 16, 1111-1119
[2]Belofsky G N, Jensen P R, Fenical W. (1999) Sansalvamide: A new cytotoxic cyclic depsipeptide produced by a marine fungus of the genus *Fusarium*. *Tetrahedron Lett.* 40, 2913-2916
[3]Cueto M, Jensen P R, Fenical W. (2000) N-Methylsansalvamide, a cytotoxic cyclic depsipeptide from a marine fungus of the genus *Fusarium Phytochemistry*. 55, 223-226
[4]Oh DC, Jensen P R, Fenical W. (2006) Zygosporamide, a cytotoxic cyclic depsipeptide from the marine-derived fungus *Zygosporium masonii*. *Tetrahedron Lett.* 47, 8625-8628

Example 3

Structural Analysis of Cyclic Depsipeptides (1) Compound A

The functional group of compound 1 was investigated by an FT IR-8400S infrared spectrophotometer (Shimadzu, Japan). IR analysis of Compound A showed amide (1654.42 cm$^{-1}$) and ester (1745.52 cm$^{-1}$) bonds (FIG. 10). The maximum UV spectrum of compound 1 was determined at 287 nm in methanol. Compound A was found to have a melting point of 82° C. as measured by a melting point apparatus (Thermo Fisher scientific Inc. Waltham. USA).

1D-NMR ($^1$H NMR, $^{13}$C NMR, and DEPT) was analyzed on a Bruker DMX 600 spectrometer system while 2D-NMR (COSY, HMQC, and HMBC) was measured on a Bruker AVANCE 800 spectrometer system. The 1D and 2D NMR spectra were collected in methanol (CD$_3$OD).

The $^1$H and $^{13}$C NMR spectral data acquired for Compound A accounted for typical resonances for a cyclic depsipeptide are shown in Table 2.

TABLE 2

| Position | 13C | 1H J in brackets | HMBC Correlations |
|---|---|---|---|
| O-Leu | | | |
| 1 | 172.254 (C) | | H2, H3, H27 |
| 2 | 75.407 (CH) | 5.191 q (4.59, 4.81) | H3 |
| 3 | 42.436 (CH2) | 1.950 m, 1.695 m | H4 |
| 4 | 25.939 (CH) | 1.695 m | H5, H6 |
| 5 | 23.253 (CH3) | 0.997 t (6.62) | H3, H4, H6 |
| 6 | 23.205 (CH3) | 0.997 t (6.62) | H3, H4, H5 |
| Leu | | | |
| 7 | 171.175 (C) | | H2, H3, H8, H9 |
| 8 | 52.895 (CH) | 4.743 q (6.01, 5.90) | H9 |
| 9 | 42.740 (CH2) | 1.876 m, 1.630 m | H8, H11, H12 |
| 10 | 26.065 (CH) | 1.379 t (7.09) | H9, H11, H12 |
| 11 | 23.436 (CH3) | 0.854 d (6.59) | H9, H12 |
| 12 | 22.049 (CH3) | 0.787 d (6.51) | H9, H10, H11 |
| Phe | | | |
| 13 | 173.887 (C) | | H8, H9, H14, H15 |
| 14 | 57.905 (CH) | 4.685 q (4.85, 4.78) | H15 |
| 15 | 39.514 (CH2) | 3.157 m | H14, H17 |

TABLE 2-continued

| Position | 13C | 1H J in brackets | HMBC Correlations |
|---|---|---|---|
| 16 | 138.803 (C) | | H19, H15 |
| 17 | 130.696 (CHx2) | 7.345 d (7.38) | H18, H19 |
| 18 | 127.811 (CH) | 7.185 t (7.28) | H17 |
| 19 | 129.528 (CHx2) | 7.257 t (7.55) | H17, H18 |
| Val | | | |
| 20 | 173.392 (C) | | H14, H21 |
| 21 | 62.408 (CH) | 4.151 d (10.17) | H22, H23, H24 |
| 22 | 31.968 (CH2) | 2.289 m | H23, H24 |
| 23 | 20.028 (CH3) | 0.956 t (6.86) | H24 |
| 24 | 19.528 (CH3) | 0.956 t (6.86) | H23 |
| Leu | | | |
| 25 | 174.247 (C) | | H21, H26, H28, H29 |
| 26 | 55.289 (CH) | 4.115 d (10.11) | H27 |
| 27 | 30.903 (CH2) | 1.290 s | H28 |
| 28 | 26.065 (CH) | 1.630 m | H29, H30 |
| 29 | 22.317 (CH3) | 0.905 q (7.14, 6.06) | H28, H30 |
| 30 | 22.411 (CH3) | 0.956 t (6.86) | H28, H29 |

Figure 12:
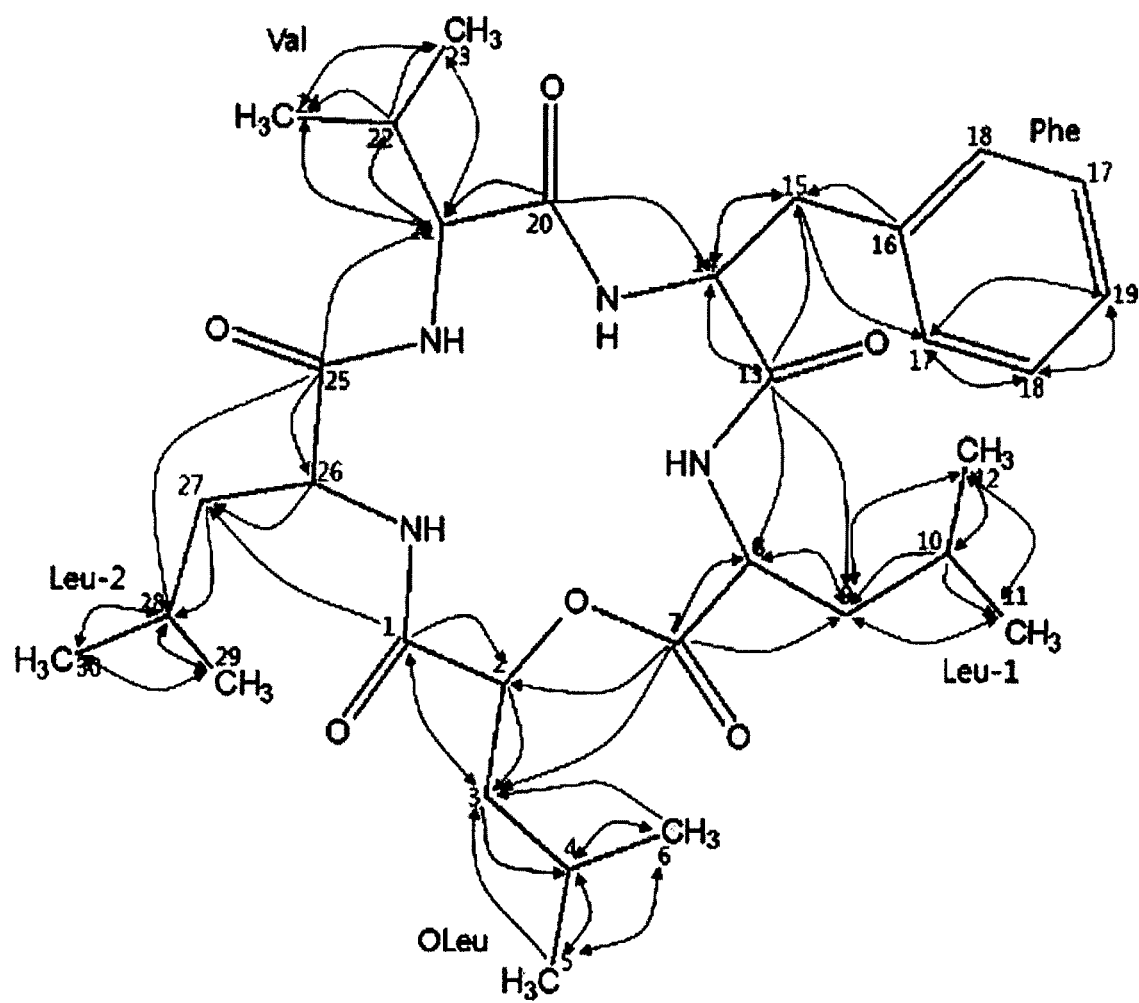
FIG. 12 is a diagram showing the HMBC correlations of compound A.

According to the DEPT and 2D NMR spectral data (COSY, HMQC, and HMBC), Compound A was composed of five units: leucic acid (OLeu), leucine (Leu), valine (Val), phenylalanine (Phe) and leucine (Leu). The sequence of the five units in Compound A was determined by analyzing HMBC correlation data (FIG. 12).

The data identified Compound A as the cyclic pentadepsipeptide of Chemical Formula 2.

[Chemical Formula 2]

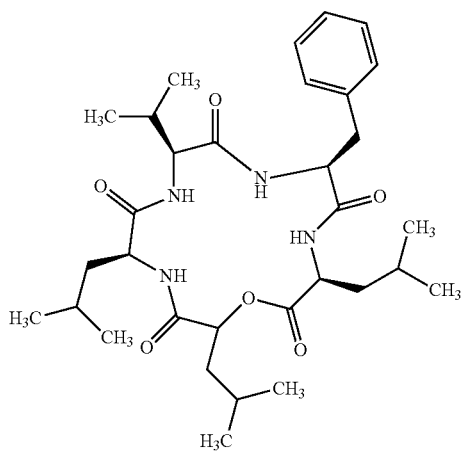

Differing from sansalvamide in the sequence of four amino acid residues and one hydroxy acid, the compound of Chemical Formula 2 was a novel cyclic pentadepsipeptide and named neo-sansalvamide.

(2) Compound B

Figure 13:
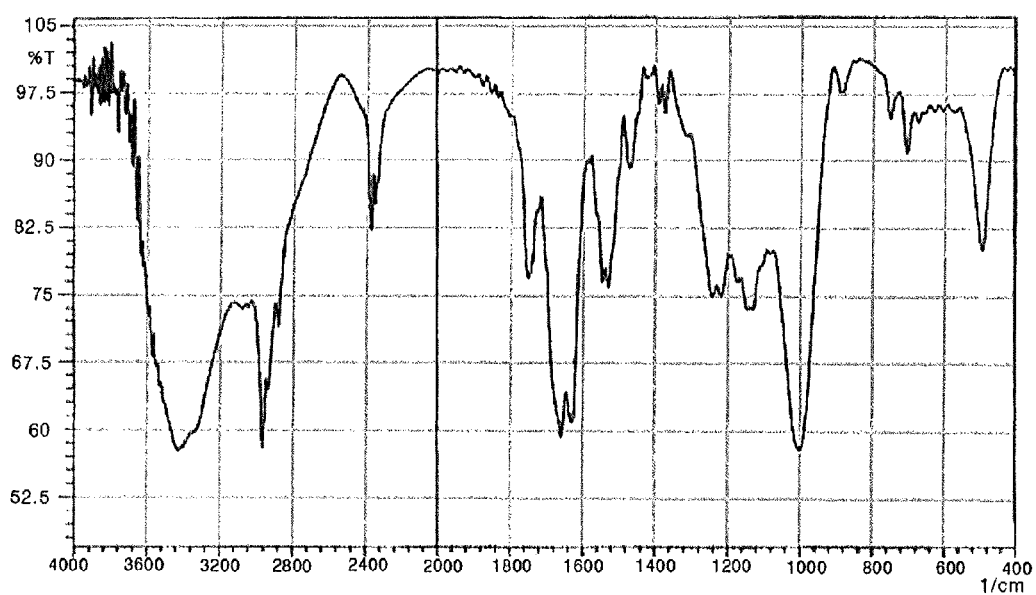
FIG. 13 is of infrared spectra of Compound B, measured by an FT IR-8400S infrared spectrophotometer.

IR spectra of Compound B showed amide (1653.24 $cm^{-1}$) and ester (1742.65 $cm^{-1}$) bonds (FIG. 13). The maximum UV spectrum was determined at 213 nm in methanol and the melting point was measured to be about 82° C.

1D-NMR ($^1$H NMR, $^{13}$C NMR, and DEPT) was analyzed on a Bruker DMX 600 spectrometer system while 2D-NMR (COSY, BMOC, and HMBC) was measured on a Bruker 600 spectrometer system. The 1D and 2D NMR spectra were collected in $CDCl_3$.

The $^1$H and $^{13}$C NMR spectral data acquired for Compound B accounted for typical resonances for a cyclic depsipeptide (Table 3).

TABLE 3

| Position | 13C | 1H J in brackets | HMBC Correlations |
|---|---|---|---|
| OLeu | | | |
| 1 | 170.313 | | H-29, H-30 |
| 2 | 75.347 | 4.970 q (3.63, 4.03) | H-3 |
| 3 | 40.814 | 1.671 m, 1.729 m | H-2, H-4 |
| 4 | 25.122 | 1.729 m | H-3 |
| 5 | 23.402 | 0.937 m | H-2, H-6 |
| 6 | 23.453 | 0.937 m | H-3, H-5 |
| Phe | | | |
| 7 | 170.949 | | H-2, H-3, H-8, H-9 |
| 8 | 54.435 | 4.803 q (5.68, 6.41) | H-9 |
| 9 | 37.359 | 3.075 q (6.01, 5.97), 3.453 q (6.59, 6.60) | H-8, H-10, H-11, H-12 |
| 10 | 136.553 | | H-8, H-9, H-11 |
| 11 | 128.975 | 7.284 m | H-12, |
| 12 | 129.496 | 7.284 m | H-11 |
| 13 | 127.393 | 7.190 d (6.79), | H-12, |
| 14 (NH) | | 6.530 d (8.78) | |
| Leu | | | |
| 15 | 170.290 | | NH-14, H-16, H-17 |
| 16 | 51.222 | 4.694 q (8.15, 8.25) | H-17, H-18, H-21 |
| 17 | 39.694 | 1.644 t (7.66, 7.26), 1.644 t (7.66, 7.26) | H-16, H-18 |
| 18 | 24.637 | 1.388 m | H-16, H-17 |
| 19b | 21.809 | 0.937 m | H-17, H-18, H-20 |
| 20b | 21.809 | 0.937 m | H-17, H-18, H-20 |
| 21 (NH) | | 7.465 d (9.07) | |
| Val | | | |
| 22 | 171.129 | | NH-21, H-23 |
| 23 | 54.416 | 4.590 q (5.61, 5.62) | H-24, H-25, H-26 |
| 24 | 30.855 | 1.991 m | H-23, H-25, H-26 |
| 25 | 17.127 | 0.833 d (6.75) | H-22, H-23, H-26 |
| 26 | 20.029 | 0.976 q (2.76, 3.21) | H-22, H-23, H-24 |
| 27 (NH) | | 6.805 d (8.78) | |
| NMeLeu | | | |
| 28 | 173.143 | | H-23, NH-27, H-29, N—Me-34 |
| 29 | 66.762 | 4.803 q (6.41, 6.31) | H-30, H-31 |
| 30 | 37.493 | 1.579 m, 1.772 m | H-29, H-31 |
| 31 | 25.528 | 1.472 m | H-29, H-30, H-32, H-33 |
| 32b | 22.390 | 0.937 m | H-30, H-31 |
| 33b | 23.143 | 0.937 m | H-31, H-32 |
| 34 (N—Me) | 40.331 | 3.180 s | H-29 |

Figure 14:
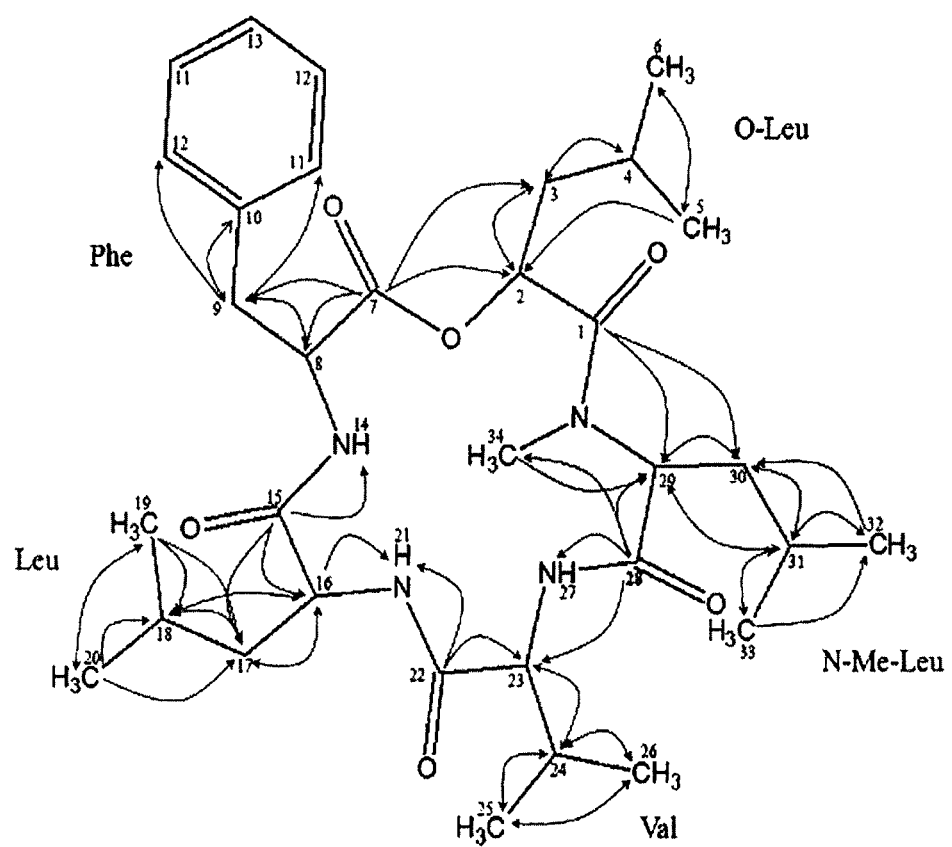
FIG. 14 is a diagram showing the HMBC correlations of compound B.

According to the DEPT and 2D-NMR spectral data (COSY, HMQC, and HMBC), Compound B was composed of five units: leucic acid (OLeu), N-methylleucine (N-MeLeu), valine (Val), phenylalanine (Phe) and leucine (Leu). The sequence of the five units in Compound B was determined by analysis of the HMBC correlation data (FIG. 14).

The data identified Compound B as the cyclic pentadepsipeptide of Chemical Formula 1.

[Chemical Formula 1]

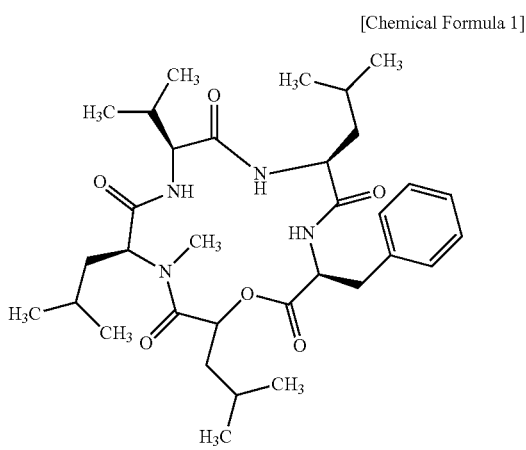

Differing from N-methylsansalvamide in the sequence of four amino acid residues and one hydroxy acid, the compound of Chemical Formula 1 was a novel cyclic pentadepsipeptide and was named neo-Nmethylsansalvamide.

(3) Determination of Stereo-Chemical Structures

Figure 15:
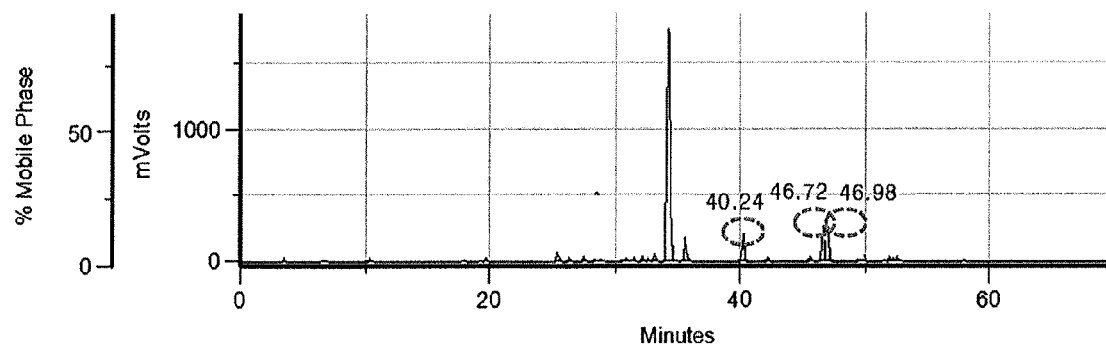
FIG. 15 is an HPLC chromatogram for determining the stereochemical structure of amino acids in Compound A.
Figure 16:
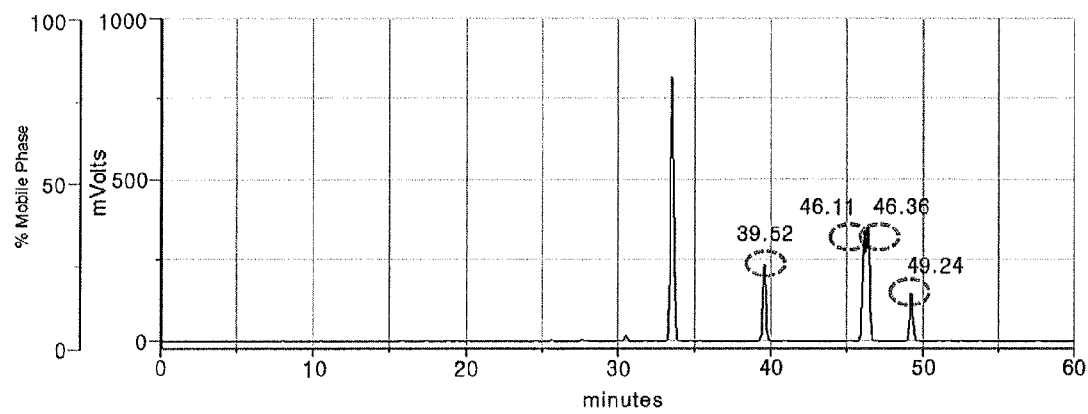
FIG. 16 is an HPLC chromatogram for determining the stereochemical structure of amino acids in Compound B.
Figure 17:
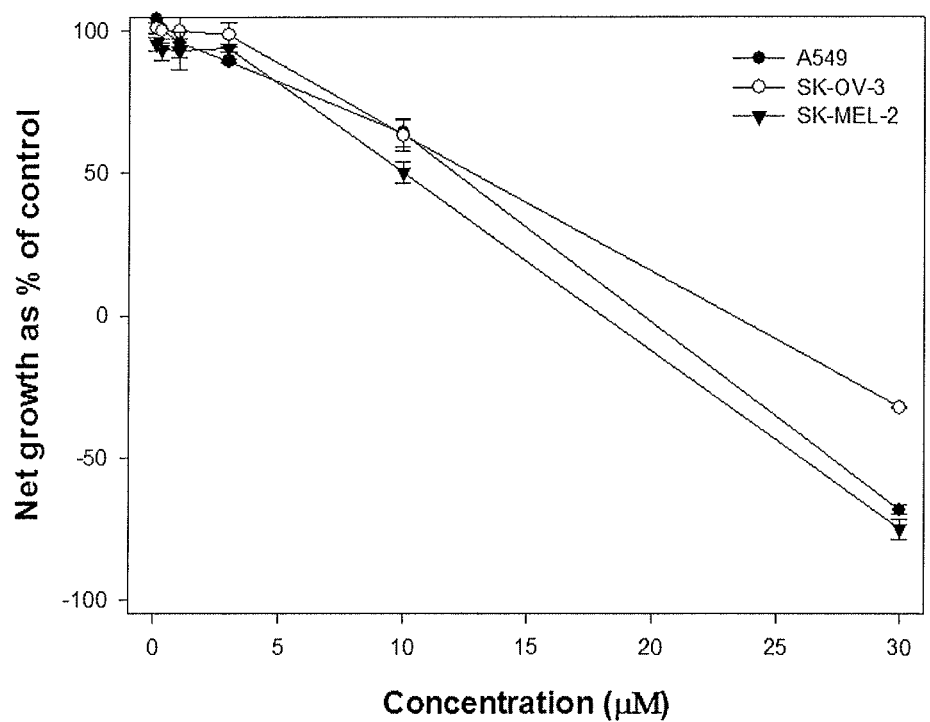
FIG. 17 is a graph showing the cytotoxic effect of the compound of Chemical Formula 1 on non-multidrug resistant cancer cell lines.
Figure 18:
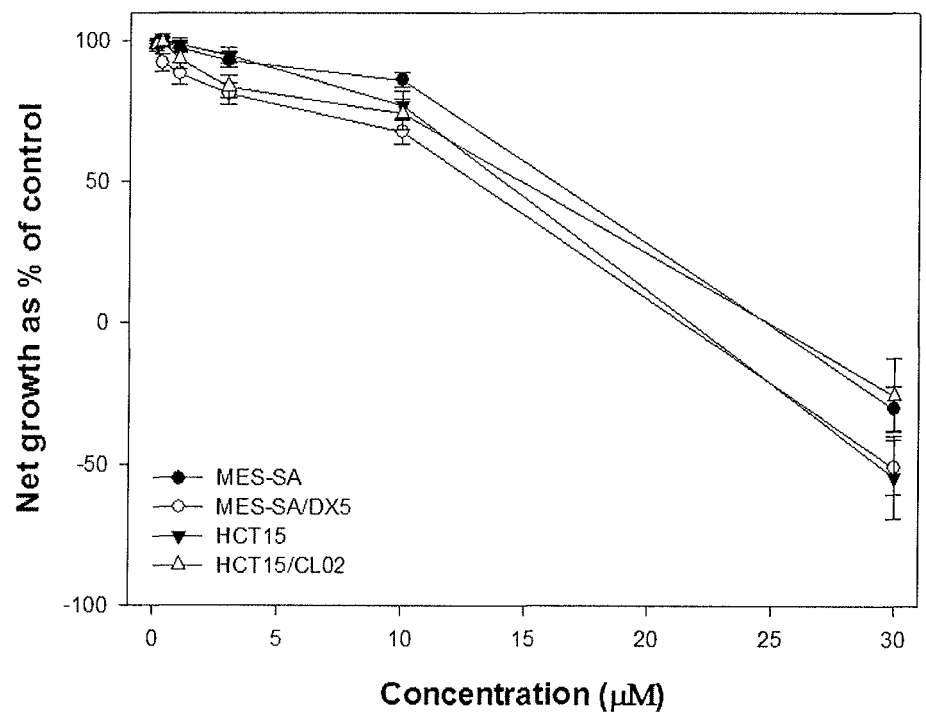
FIG. 18 is a graph showing the cytotoxic effect of the compound of Chemical Formula 1 on multidrug resistant cancer cell lines.
Figure 19:
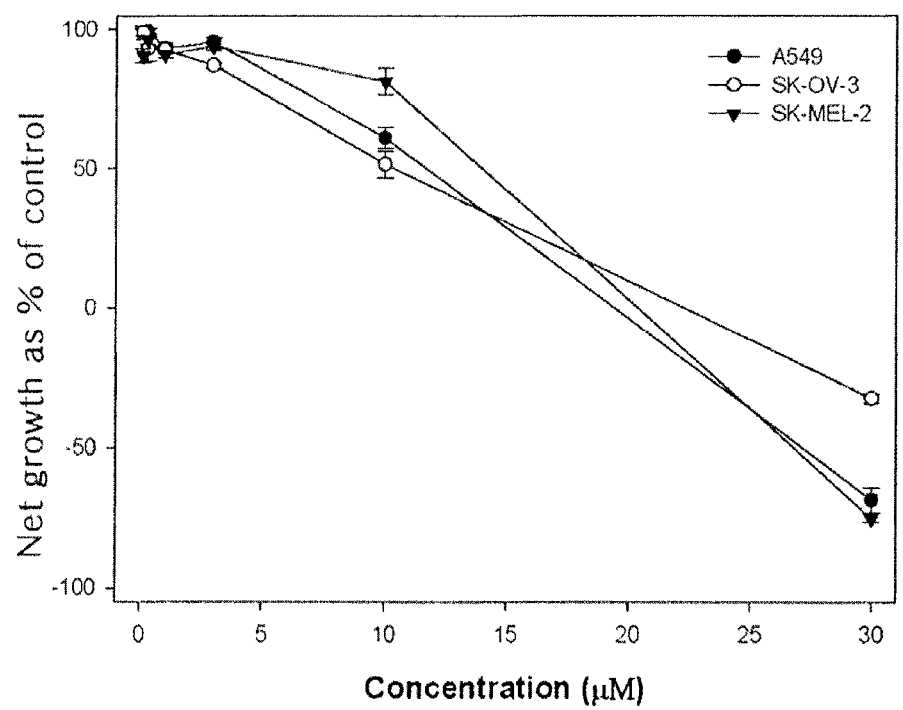
FIG. 19 is a graph showing the cytotoxic effect of the compound of Chemical Formula 2 on non-multidrug resistant cancer cell lines.
Figure 20:
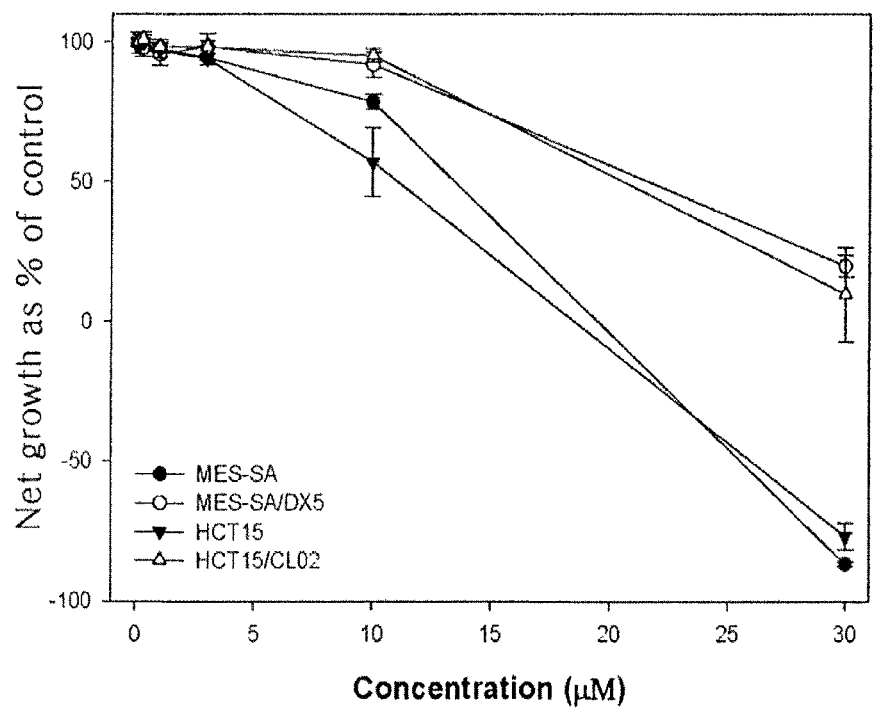
FIG. 20 is a graph showing the cytotoxic effect of the compound of Chemical Formula 2 on non-multidrug resistant cancer cell lines.
Figure 21:
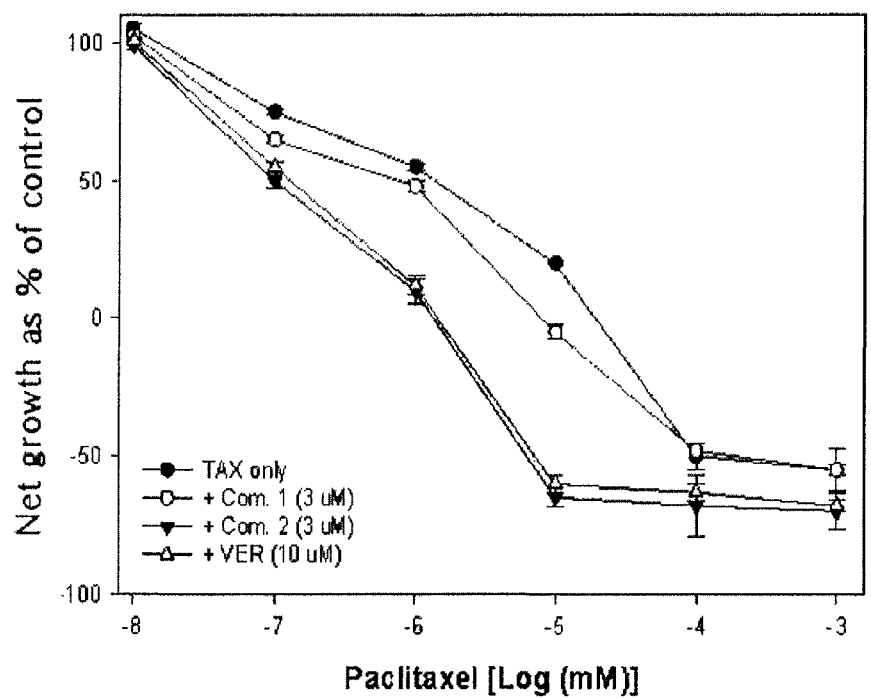
FIG. 21 is a graph showing the multidrug resistance-reversing activity of the compounds of Chemical Formulas 1 and 2 against the HCT15 cell line.
Figure 22:
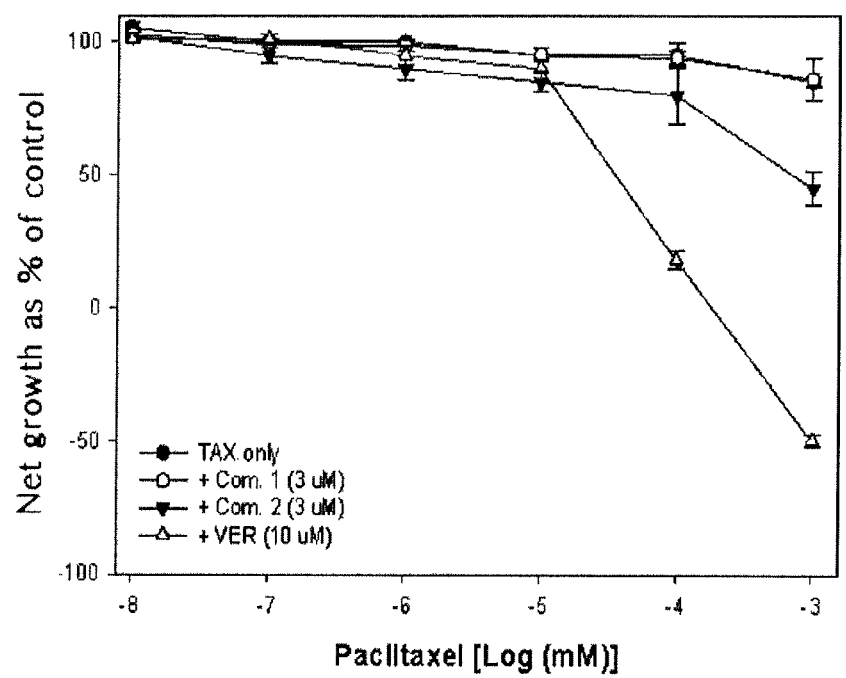
FIG. 22 is a graph showing the multidrug resistance-reversing activity of the compounds of Chemical Formulas 1 and 2 against the HCT15/CL02 cell line.
Figure 23:
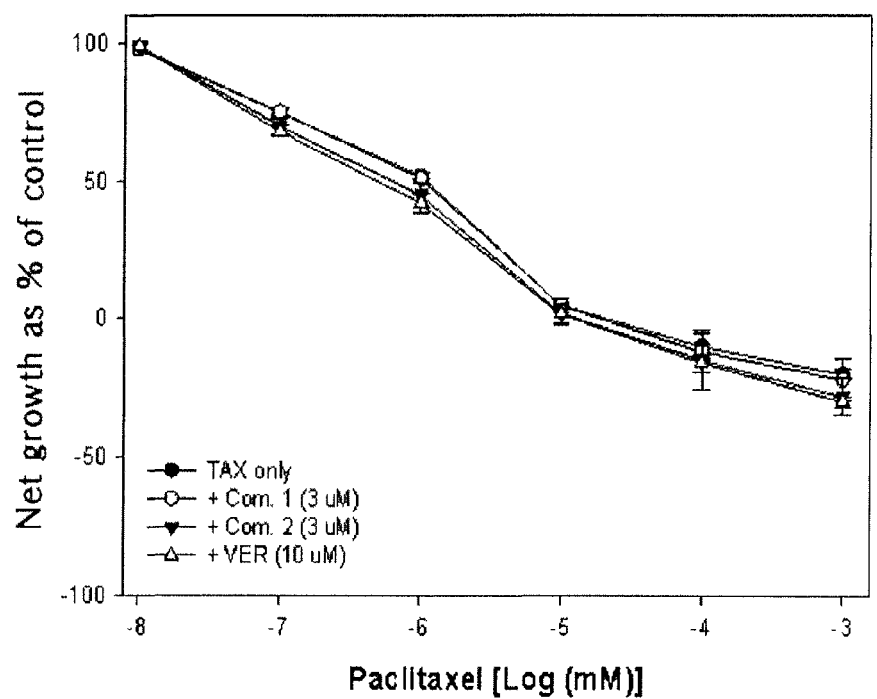
FIG. 23 is a graph showing the multidrug resistance-reversing activity of the compounds of Chemical Formulas 1 and 2 against the MEA-SA cell line.
Figure 24:
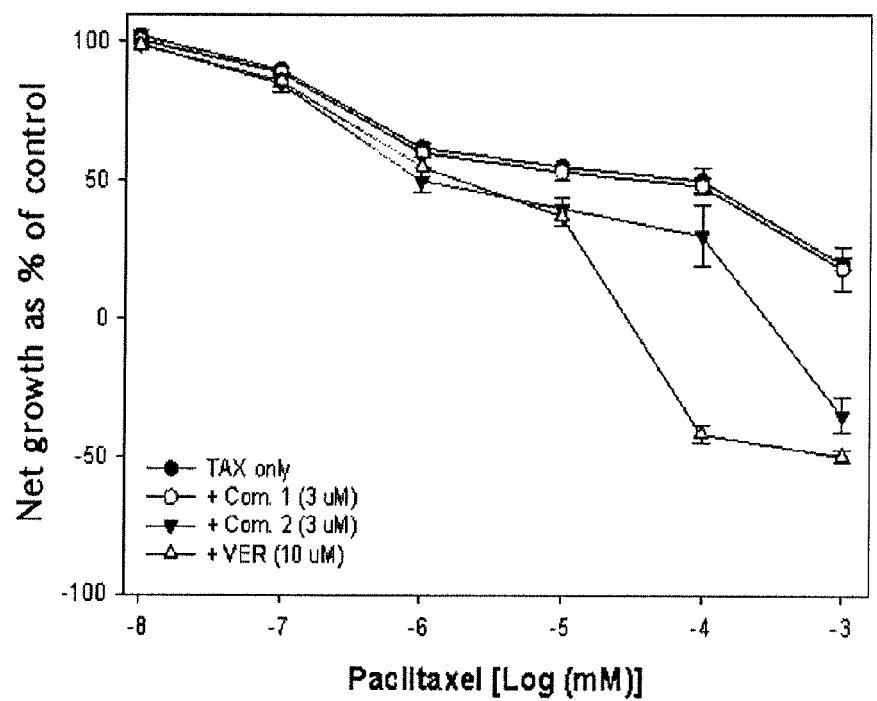
FIG. 24 is a graph showing the multidrug resistance-reversing activity of the compounds of Chemical Formulas 1 and 2 against the MEA-SA/DX5 cell line.

The absolute stereo-chemistries of amino acids in Compounds A and B were determined by acid hydrolysis, followed by the derivation of the amino acids with Marfeys' Reagent and HPLC analysis. The amino acids were identified by co-injection with authentic amino acid standards. The results are given in FIGS. 15 (Compound A) and 16 (Compound B). The amino acids in Compounds A and B were all shown to possess L configurations.

Example 4

Cytotoxicity

Known cyclic hexadepsipeptides (beauvericin, enniatin H, I, and MK1688) and the compounds of Chemical Formulas 1 and 2 were evaluated for in vitro cytotoxicity against various non-multidrug-resistant human cancer cell lines and multidrug-resistant cancer cell lines using the SRB method.

Human non-small-cell lung cancer cell line (A549) ovarian cancer cell line (SK-OV-3), skin cancer cell line (SK-MEL-2), and uterine sarcoma cell line MES-SA and its multi-drug resistant subline (MES-SA/DX5) were purchased from the American Type Culture Collection (USA). Colorectal carcinoma cancer cell line (HCT-15) was provided by the National Cancer Institute (NCI). HCT15/CL02 cell lines were established from HCT15 cells by continuous and stepwise exposure of the cells to doxorubicin in the Korea Research Institute of Chemical Technology (Korea). The inhibitory activities were quantified as the concentration required for inhibiting cell growth in vitro by 50% ($EC_{50}$) under the assay conditions, with doxorubicin serving as a control.

TABLE 4

| Sample | EC50 (μM) | | |
|---|---|---|---|
| | A549 | SK-OV-3 | SK-MEL-2 |
| BEA | 1.43 ± 0.16 | 1.39 ± 0.09 | 1.47 ± 0.09 |
| EN H | 1.84 ± 0.11 | 1.71 ± 0.03 | 1.77 ± 0.03 |
| EN I | 0.50 ± 0.04 | 0.49 ± 0.03 | 0.53 ± 0.06 |
| EN MK1688 | 0.45 ± 0.04 | 0.46 ± 0.03 | 0.63 ± 0.01 |
| Com. 1 | 11.70 ± 0.55 | 10.38 ± 0.64 | 13.99 ± 1.32 |
| Com. 2 | 10.73 ± 0.15 | 11.24 ± 1.23 | 10.02 ± 0.53 |
| Doxorubicin | 0.03 ± 0.01 | 0.06 ± 0.01 | 0.04 ± 0.01 |

TABLE 5

| Sample | EC50 (μM) | | | |
|---|---|---|---|---|
| | MES-SA | MES-SA/DX5 | HCT15 | HCT15/CL02 |
| BEA | 1.29 ± 0.02 | 1.34 ± 0.03 | 1.53 ± 0.09 | 1.66 ± 0.08 |
| EN H | 12.94 ± 0.23 | 14.89 ± 0.59 | 16.74 ± 0.96 | 17.71 ± 0.49 |
| EN I | 3.94 ± 0.03 | 4.90 ± 0.27 | 5.56 ± 0.22 | 5.88 ± 0.21 |
| EN MK1688 | 13.62 ± 1.05 | 13.59 ± 0.79 | 14.02 ± 0.54 | 16.35 ± 0.84 |
| Com. 1 | 11.75 ± 0.13 | 19.45 ± 1.10 | 9.95 ± 1.00 | 22.08 ± 2.45 |
| Com. 2 | 13.96 ± 0.74 | 11.42 ± 0.30 | 12.46 ± 0.71 | 13.50 ± 1.19 |
| Doxorubicin | 0.01 ± 0.0001 | 1.03 ± 0.31 | 0.01 ± 0.001 | 4.48 ± 2.15 |

Belofsky et al. reported that sansalvamide was responsible for the majority of the cancer cell cytotoxicity present in the crude extract, exhibiting an in vitro $IC_{50}$ value of 9.8 μg/ml toward HCT-116 colon carcinoma [Belofsky et al., 1999]. Ceuto et al. (2000) reported that N-Methylsansalvamide exhibited in vitro cytotoxicity in the NCI human tumor cell line screen ($GI_{50}$ 8.3 μM) [Ceuto et al., 2000]. As is apparent from the data of Tables 4 and 5, the cyclic pentadepsipeptides of Chemical Formulas 1 and 2 exhibit cytotoxicity against most cell lines as potent as that of sansalvamide A or N-methylsansalvamide irrespective of the possession of multidrug resistance. The cyclic pentadepsipeptide of Chemical Formula 1 was of more potent inhibitory activity against MDR cancer lines than was that of Chemical Formula 2 (FIGS. 17 to 20).

Example 5

Multidrug Resistance-Reversing Activity

The cyclic pentadepsipeptides of Chemical Formulas 1 and 2 were analyzed for MDR-reversing activity by comparing inhibitory activities against multidrug-resistant cancer cell lines (MES-SA/DX5 and HCT15/CL02) with those against non-multidrug-resistant cancer cell lines (MES-SA and HCT15). In this regard, the effects of the cyclic pentadepsipeptides of Chemical Formulas 1 and 2 on paclitaxel's cytotoxicity against MDR tumor cells were measured (Table 6). Verapamil (VER), an MDR-reversing agent with inhibitory activity against P-glycoprotein, was used as a control.

TABLE 6

| Sample | EC50 (nM) | | | |
|---|---|---|---|---|
| | MES-SA | MES-SA/DX5 | HCT15 | HCT15/CL02 |
| TAX | 1.00 ± 0.20 | 10.00 ± 0.53 | 0.85 ± 0.63 | >1,000 |
| Com. 1(3 µM) | 1.00 ± 0.30 | 6.31 ± 0.91 | 0.39 ± 0.08 | >1,000 |
| Com. 2(3 µM) | 1.00 ± 0.30 | 1.58 ± 0.12 | 0.10 ± 0.02 | 288.40 ± 21.02 |
| VER (10 µM) | 1.00 ± 0.10 | 1.78 ± 0.33 | 0.11 ± 0.05 | 33.89 ± 8.42 |

The cyclic pentadepsipeptide of Chemical Formula 2 increased the cytotoxicity of paclitaxel against MDR cell lines, but only slightly. On the other hand, the cyclic pentadepsipeptide of Chemical Formula 1 remarkably enhanced the cytotoxicity of paclitaxel (FIGS. 21 to 24). Therefore, the N-methyl group in the cyclic pentadepsipeptide may be a factor crucial for the expression of the MDR reversal activity. The MDR-reversing activity of the cyclic pentadepsipeptide of Chemical Compound 1 was similar to that of the positive control verapamil.

Example 6

Anti-Bacterial and Anti-Fungal Activities (1) Anti-Bacterial Activity

Assays for antibacterial activity were performed with 3 Gram-positive (*Listeria monocytogenes* ATCC 14028, *Staphylococcus aureus* ATCC 35556 and *Bacillus cereus* ATCC 13061) and 3 Gram-negative bacteria (*Escherichia coli* ATCC 8739, *Pseudomonas aeruginosa* ATCC 9026 and *Salmonella typhimurium* ATCC 14028). Each of the compounds of Chemical Formulas 1 and 2 was dissolved in different concentrations (0.1, 0.5, 1, and 2 mM) in dimethyl sulfoxide (DMSO). The solutions were applied to a sterile paper disc (5 mm diameter), followed by evaporating the DMSO solvent. Bacteria was inoculated at a density of 1×10$^7$ CFU/ml on Tryptic soy agar (TSA) and then, the paper disc was placed on the bacteria-inoculated agars. After incubation at 37° C. for 24 hr, the clear zone around each disc was observed and its diameter was measured.

Neither the compound of Chemical Formula 1 nor Chemical Formula 2 showed inhibitory activity against all of the bacteria tested.

(2) Anti-Fungal Activity

Inhibitory activity was performed against four fungus strains (*Mucor rouxii, Penicillium citrinum, Fusarium oxysporum*, and *Aspergillus oryzae*).

Drops of 1 and 10 mM solutions of compounds of Chemical Formulas 1 and 2 in methanol were loaded onto sterile paper discs (8 mm diameter) and the methanol solvent was evaporated under a hood. The paper discs were placed on fungus mycelia grown on potato dextrose agar. After incubation at 25° C. for 48 hr, clear zones around the discs were observed and their diameters were measured. A filter treated with pure methanol was used as a negative control.

Figure 25:
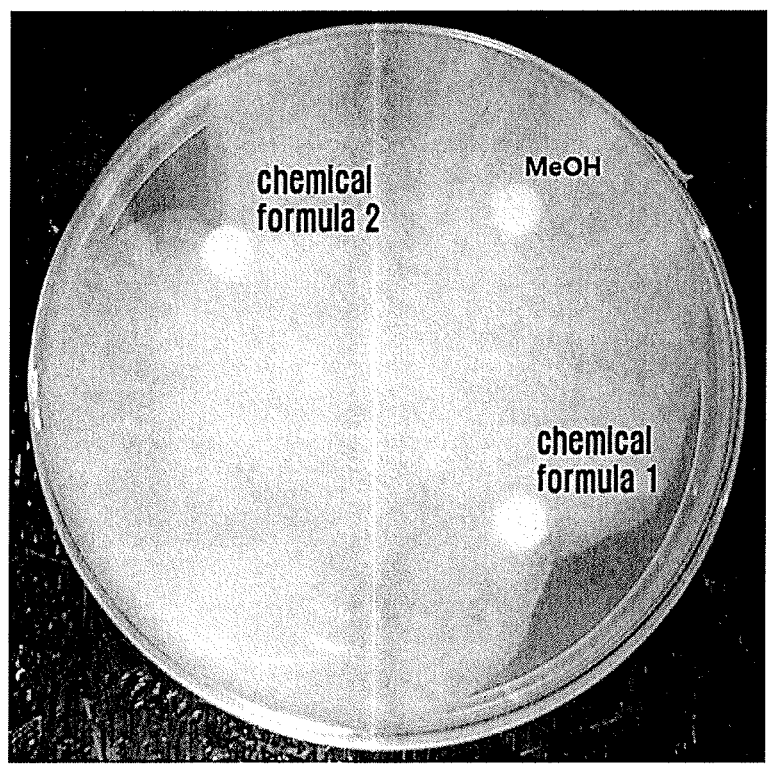
FIG. 25 is a photograph showing the anti-fungal activity of the compounds of Chemical Formulas 1 and 2 against Mucor rouxii grown on PDA, with 10 mM of compounds of Chemical Formulas 1 and 2 placed thereon.
Figure 26:
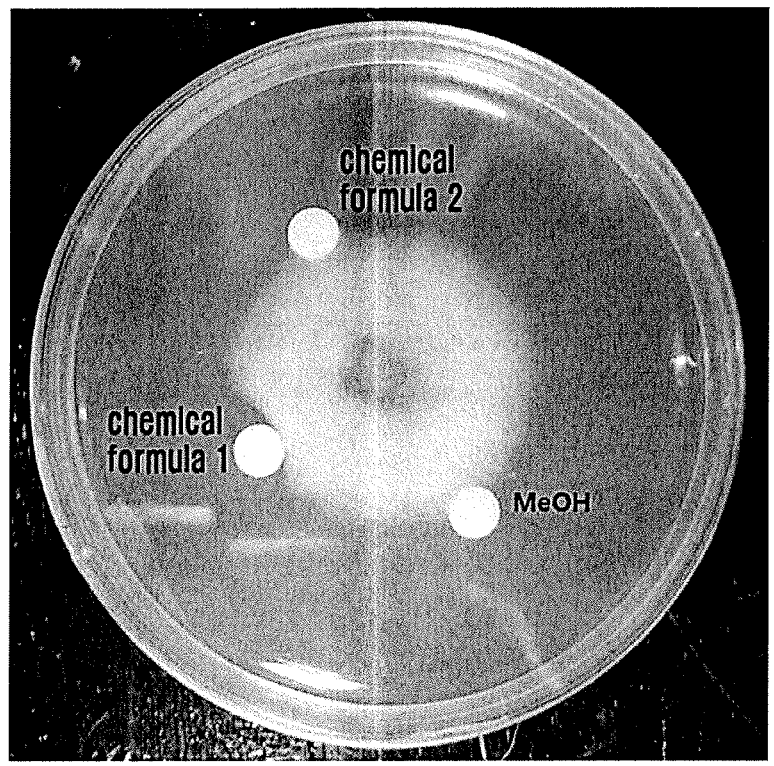
FIG. 26 is a photograph showing the anti-fungal activity of the compounds of Chemical Formulas 1 and 2 against Fusarium oxysporum grown on PDA, with 10 mM of compounds of Chemical Formulas 1 and 2 placed thereon.
Figure 28:
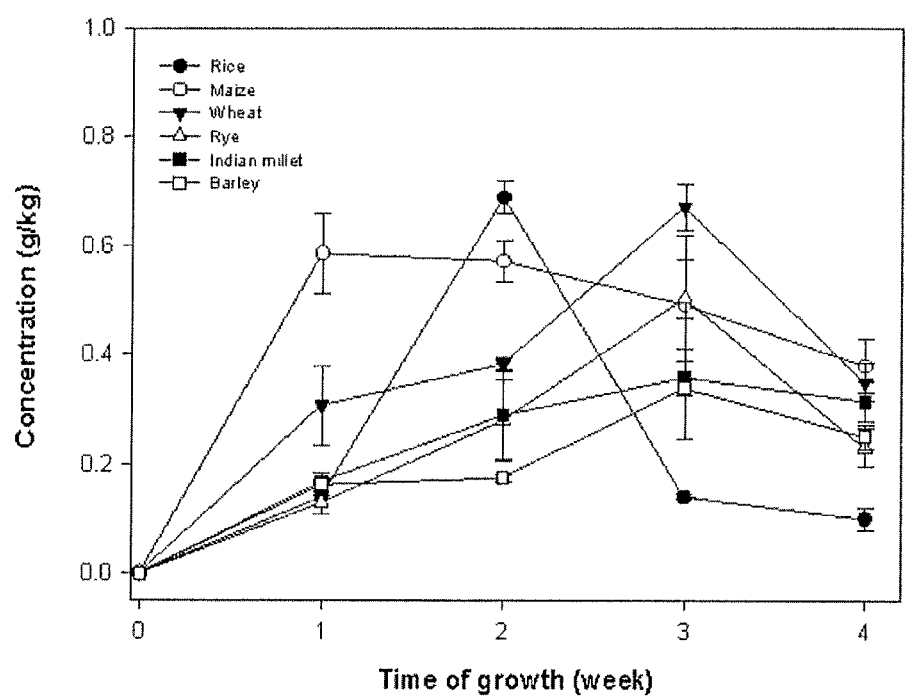
FIG. 28 is a graph in which the produced amounts of the compound of Chemical Formula 2 are plotted against the time of growth for six different cereal media.

The inhibitory effects of compounds purified from *F. solani* KCCM 90040 on the mycelial growth of four fungal strains (*Mucor rouxii, Penicillium citrinum, Fusarium oxysporum*, and *Aspergillus oryzae*) are shown in FIG. 28. The results of the antifungal tests revealed that compound 1 and 2 were inhibitory against *Mucor rouxii*, and *Fusarium oxysporum*, weakly. No inhibitory activities were detected at 1 mM of the compound of Chemical Formula 1 or 2 against all of the four fungal strains. At 10 mM of the compounds of Chemical Formulas 1 and 2, no clear zones were observed on the agar in which *Mucor rouxii* was grown, but the hyphal growth of *Mucor rouxii* was reduced near the purified compounds containing paper disc (FIG. 25). While the compound of Chemical Formula 2 did not produce a clear zone on the mycelium of *Fusarium oxysporum* at 10 mM, the compound of Chemical Formula 1 exhibited an inhibitory effect at 10 mM, weakly (FIG. 26).

Example 7

Selection of Cereal Medium

Figure 27:
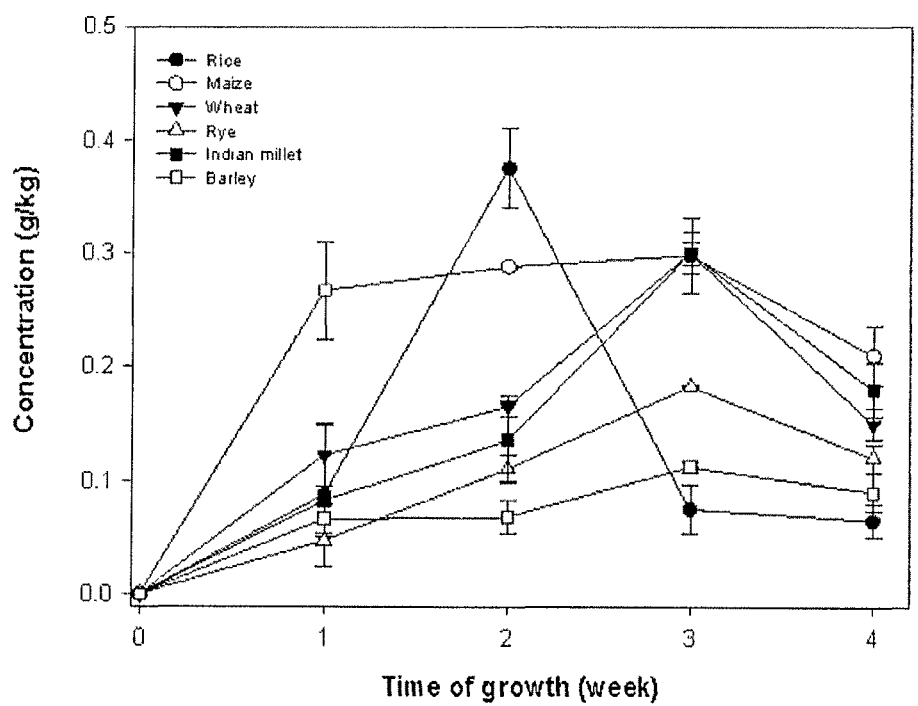
FIG. 27 is a graph in which the produced amounts of the compound of Chemical Formula 1 are plotted against the time of growth for six different cereal media.

*Fusarium solani* KCCM90040 was inoculated at a density of 1×10$^5$ spores/mL on a cereal medium which was prepared from 50 g of an autoclaved cereal substance with the water content thereof adjusted to 40 wt % with sterile distilled water. The microorganism was grown at 25° C. during which the medium was shaken once a day. The production of the compounds of Chemical Formulas 1 and 2 by *F. solani* KCCM 90040 upon culturing on six different solid cereal substrates is quantitatively depicted in FIGS. 27 and 28, respectively.

The production of the compound of Chemical Formula 2 peaked on the 2$^{th}$ week after incubation on rice (Avg. 0.375 g/kg). The use of maize, wheat or Indian millet, instead of rice, decreased the productivity of the compound of Chemical Formula 2 by about 80%. Particularly low production (0.112 g/kg) was observed on barley.

As for the compound of Chemical Formula 1, its maximal production was obtained on the 2$^{th}$ week after incubation on rice (Avg. 0.689 g/kg). On the 3$^{rd}$ week after the incubation on wheat, its production peaked to 0.672 g/kg. Replacement of rice by maize or rye decreased the production of the compound of Chemical Formula 1 by about 25%. The final production of the compound of Chemical Formula 1 on rice was twice as great as that on Indian millet or barley.

Example 8

Determination of Culture Conditions

The experimental data for the production of the compounds of Chemical Formulas 1 and 2 from *F. solani* KCCM 90040 in different treatment conditions are given in Table 7, below.

TABLE 7

| Run | Temp. | Moisture % | Time | com. 1 (g/kg) | com. 2 (g/kg) |
| --- | --- | --- | --- | --- | --- |
| 1 | 15 | 30 | 20 | 0.005 | 0.010 |
| 2 | 35 | 40 | 15 | 0.136 | 0.262 |
| 3 | 35 | 30 | 20 | 0.115 | 0.230 |
| 4 | 35 | 30 | 20 | 0.124 | 0.248 |
| 5 | 25 | 40 | 20 | 0.300 | 0.522 |
| 6 | 15 | 50 | 10 | 0.001 | 0.005 |
| 7 | 25 | 40 | 15 | 0.376 | 0.580 |
| 8 | 25 | 40 | 15 | 0.400 | 0.772 |
| 9 | 25 | 50 | 15 | 0.332 | 0.480 |
| 10 | 25 | 40 | 15 | 0.380 | 0.628 |
| 11 | 25 | 40 | 15 | 0.432 | 0.702 |
| 12 | 25 | 40 | 15 | 0.416 | 0.802 |
| 13 | 35 | 50 | 10 | 0.024 | 0.068 |
| 14 | 15 | 30 | 10 | 0.002 | 0.003 |
| 15 | 25 | 40 | 15 | 0.350 | 0.624 |
| 16 | 25 | 30 | 15 | 0.320 | 0.508 |
| 17 | 35 | 50 | 20 | 0.005 | 0.080 |
| 18 | 25 | 40 | 10 | 0.250 | 0.200 |
| 19 | 15 | 40 | 15 | 0.008 | 0.050 |
| 20 | 15 | 50 | 20 | 0.005 | 0.009 |

When cultured in a seawater-based medium, marine *Fusarium* strains were reported to produce sansalvamide in an amount of about 0.642 g/17 L [Belofsky G N, Jensen P R, Fenical W. (1999) Sansalvamide: A new cytotoxic cyclic depsipeptide produced by a marine fungus of the genus *Fusarium*. *Tetrahedron Lett.* 40, 2913-2916]. It was also reported that N-methylsansalvamide produced by the *Fusarium* strain CNL-619 reached 3.1 mg/L in a seawater-based medium [Cueto M, Jensen P R, Fenical W. (2000) N-Methylsansalvamide, a cytotoxic cyclic depsipeptide from a marine fungus of the genus *Fusarium*. *Phytochemistry.* 55, 223-226].

Variables for the production of the novel compounds of Chemical Formulas 1 and 2 upon incubation on rice were determined to specify 20~30° C. for culture temperature, 20~50% for RH, and 10~20 days for growth period, preferably 23~28° C. for culture temperature, 35~45% for RH, and 13~18 days.

Figure 29:
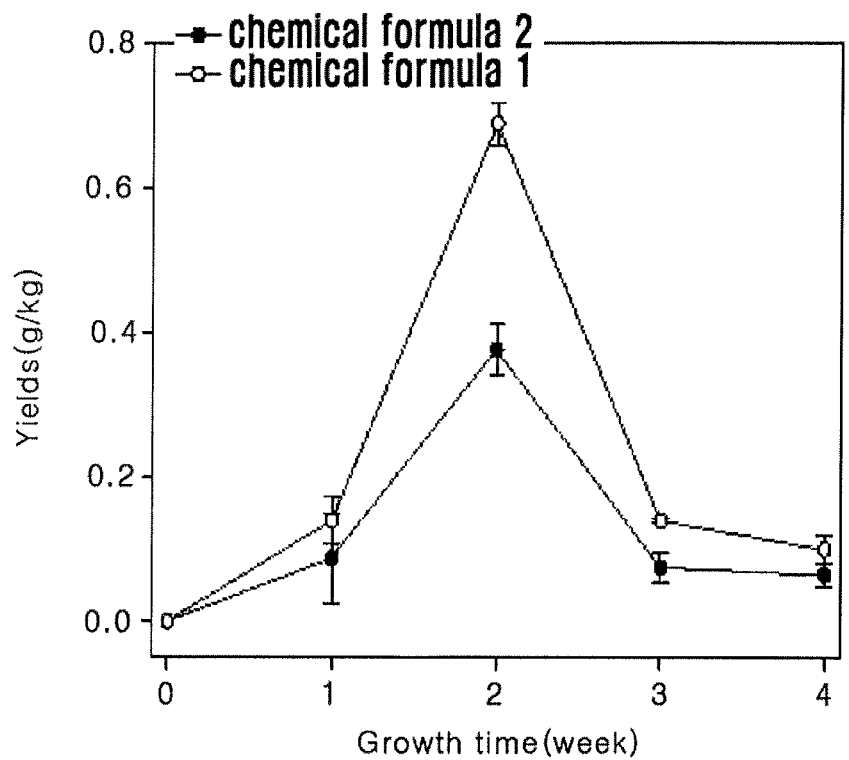
FIG. 29 is a graph showing the production of the compounds of Chemical Formulas 1 and 2 with the time of growth.
Figure 30:
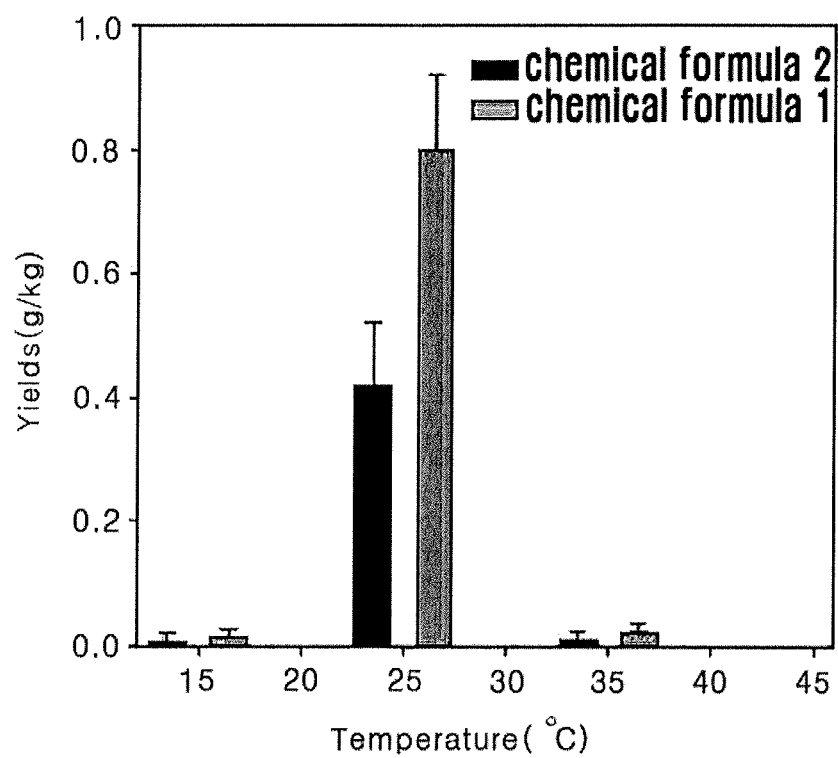
FIG. 30 is a graph showing the production of the compounds of Chemical Formulas 1 and 2 with culture temperature.
Figure 31:
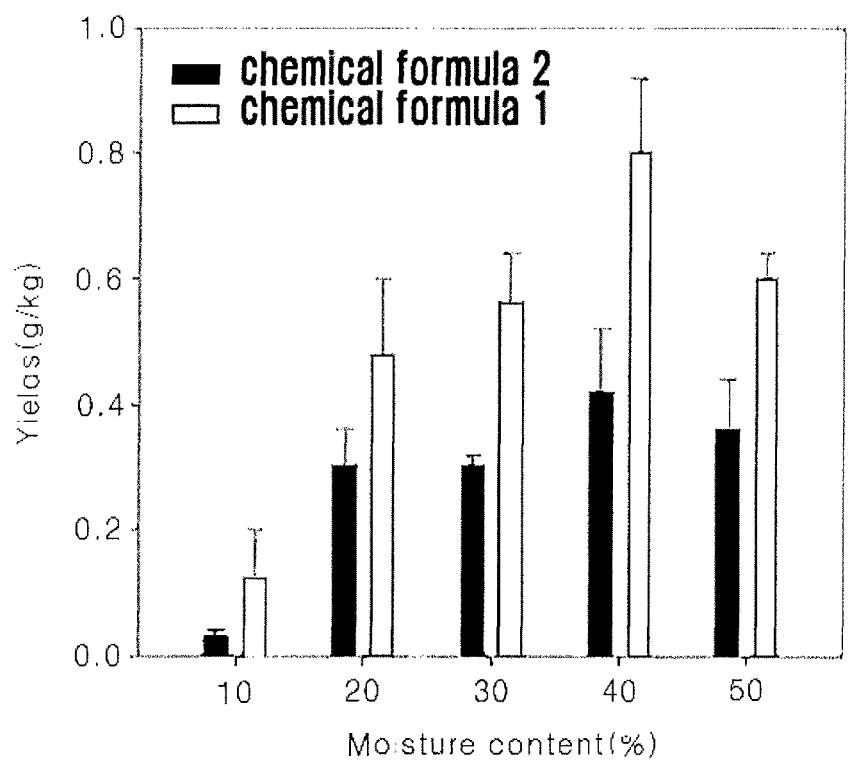
FIG. 31 is a graph showing the production of the compounds of Chemical Formulas 1 and 2 with moisture content.

Optimally, the microorganisms were cultured at 25.84° C. and 37.99 RH % for 16.03 days for optimal production of the cyclic pentadepsipeptide of Chemical Formula 1 (FIGS. 29 to 31) and at 25.87° C. and 33.87 RH % for 15.58 days for the optimal production of the cyclic pentadepsipeptide of Chemical Formula 2. Under the optimal conditions, the production was measured to be about 0.40 g/kg for the cyclic pentadepsipeptide of Chemical Formula 1 and about 0.70 g/kg for the cyclic pentadepsipeptide of Chemical Formula 2.

Formulation Example 1

Preparation of Tablet

Ingredients and Amounts

| | |
| --- | --- |
| Cyclic pentadepsipeptide of Chemical Formula 1 or 2 | 100 mg |
| Corn Starch | 68 mg |
| Lactose | 90 mg |
| Microcrystalline Cellulose | 40 mg |
| Mg Stearate | 2 mg |

The ingredients were added in the given amounts, homogeneously mixed together and granulized. The granules were prepared into tablets, each containing 100 mg of the cyclic pentadepsipeptide of Chemical Formula 1 or 2, according to a typical method.

Formulation Example 2

Preparation of Injection

Ingredients and Amounts

| | |
| --- | --- |
| Cyclic pentadepsipeptide of Chemical Formula 1 or 2 | 50 mg |
| Na metabisulfite | 1.5 mg |
| Methyl paraben | 1.0 mg |
| Propyl paraben | 0.1 mg |
| Pure water for injection | q.s. |

The ingredients were dissolved in the given amounts in boiling water with stirring cooled and loaded into 2 mL sterile vials and supplemented with injection water to form a total volume of 2 mL to afford injections, each containing 50 mg of the cyclic pentadepsipeptide of Chemical Formula 1 or 2.

Formulation Example 3

Preparation of Syrup

Ingredients and Amounts

| | |
| --- | --- |
| Cyclic pentadepsipeptide of Chemical Formula 1 or 2 | 200 mg |
| Concentrated fruit juice | 2 g |
| Sucrose | 5 g |
| Sodium citrate | 100 mg |
| Fragrant | 70 mg |
| Water | q.s. |

According to a typical method, the ingredients were mixed in the given amounts, dissolved in water with heating, cooled and loaded into vessels, each containing 200 mg of Cyclic pentadepsipeptide of Chemical Formula 1 or 2, to afford syrups.

Exhibiting cytotoxicity against a wide range of cancer cell lines, as described hitherto, the cyclic pentadepsipeptides of the present invention can be used as therapeutics for tumors. Further, they are useful as multidrug resistance inhibitors. These novel cyclic pentadepsipeptides are produced by the *Fusarium* strains of the present invention.

The invention claimed is:

1. A method for preventing or treating a cancer disease in a subject in need thereof, said method comprising administering to the subject a pharmaceutical composition comprising an effective amount of an isolated cyclic pentadepsipeptide of the following Chemical Formula I or an isolated cyclic pentadepsipeptide of the following Chemical Formula II:

[Chemical Formula 1]

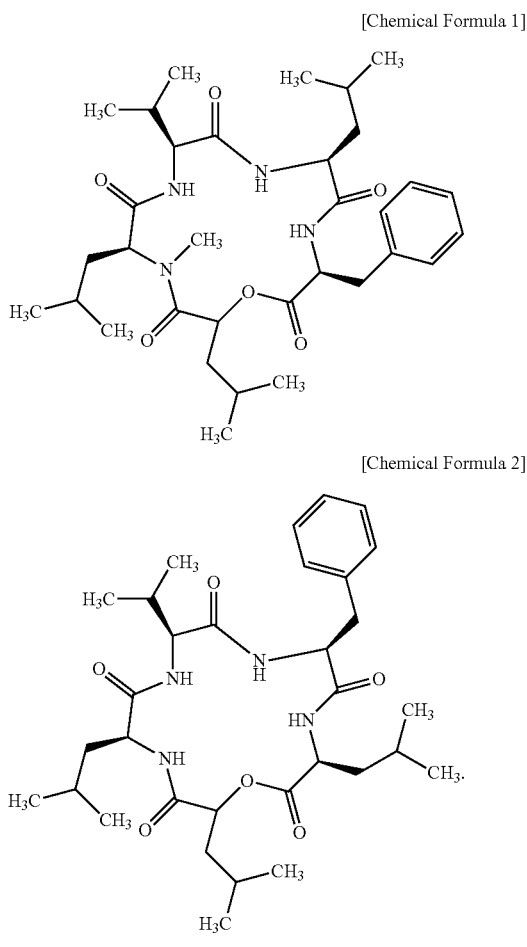 [SMILES: CC(C)CC1OC(=O)[C@H](Cc2ccccc2)NC(=O)[C@H](CC(C)C)NC(=O)[C@H](C(C)C)NC(=O)[C@H](CC(C)C)N(C)C1=O ; CC(C)CC1OC(=O)[C@H](CC(C)C)NC(=O)[C@H](Cc2ccccc2)NC(=O)[C@H](C(C)C)NC(=O)[C@H](CC(C)C)NC1=O]

[Chemical Formula 2]

2. The method according to claim 1, wherein the cyclic pentadepsipeptide is obtained from a culturing bacterial cell of the genus *Fusarium solani* strain KCCM90040 (accession No. KCCM10881P).

3. The method according to claim 1, wherein the cancer disease is skin tumors, blood tumors, lymphoma, gynecologic tumors, urologic tumors, soft tissue sarcoma, osteo- or non-osteosarcoma, breast tumors, pituitary tumors, thyroid gland tumors, adrenal cortex tumors, gastrointestinal tumors, pancreatic tumors, liver tumors, larynx tumors, papilloma or lung tumors.

4. A method for preventing or treating a multidrug resistance in a subject in need thereof, said method comprising administering to the subject a pharmaceutical composition comprising an effective amount of an isolated cyclic pentadepsipeptide of the following Chemical Formula I or an isolated cyclic pentadepsipeptide of the following Chemical Formula II:

[Chemical Formula 1]

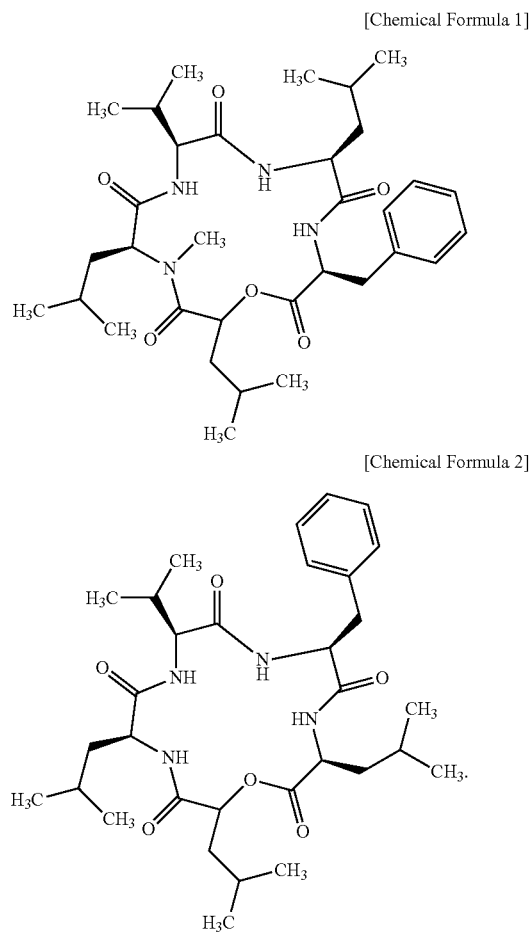 [SMILES: CC(C)CC1OC(=O)[C@H](Cc2ccccc2)NC(=O)[C@H](CC(C)C)NC(=O)[C@H](C(C)C)NC(=O)[C@H](CC(C)C)N(C)C1=O ; CC(C)CC1OC(=O)[C@H](CC(C)C)NC(=O)[C@H](Cc2ccccc2)NC(=O)[C@H](C(C)C)NC(=O)[C@H](CC(C)C)NC1=O]

[Chemical Formula 2]

5. The method according to claim 1, wherein
the cyclic pentadepsipeptide is obtained from a culturing bacterial cell of the genus *Fusarium solani* strain KCCM90040 (accession No. KCCM10881P).

6. The method according to claim 4, wherein
the multidrug resistance is multidrug resistance cancer.

* * * * *